United States Patent
Roe et al.

(10) Patent No.: US 10,493,263 B2
(45) Date of Patent: Dec. 3, 2019

(54) ONYCHOMYCOSIS TREATMENT SYSTEM AND METHOD

(71) Applicant: DEVICEFARM, INC., Newark, CA (US)

(72) Inventors: Jeffrey N Roe, Pleasanton, CA (US); Timothy C Grammer, Pleasant Hill, CA (US); Eric Tridas, St. Petersburg, FL (US); Raul Ignacio Barrera-Barraza, Fremont, CA (US); Joel Sterling Douglas, Bonita Springs, FL (US)

( * ) Notice: Subject to any disclaimer, the term of this patent is extended or adjusted under 35 U.S.C. 154(b) by 0 days.

(21) Appl. No.: 15/674,120

(22) Filed: Aug. 10, 2017

(65) Prior Publication Data

US 2017/0354815 A1    Dec. 14, 2017

Related U.S. Application Data

(63) Continuation-in-part of application No. 15/464,761, filed on Mar. 21, 2017, now Pat. No. 10,039,723, which is a continuation-in-part of application No. 14/963,552, filed on Dec. 9, 2015, now Pat. No. 10,039,782.

(60) Provisional application No. 62/089,945, filed on Dec. 10, 2014.

(51) Int. Cl.

| | |
|---|---|
| *A61N 1/04* | (2006.01) |
| *A61N 1/44* | (2006.01) |
| *A61K 31/02* | (2006.01) |
| *A61K 33/04* | (2006.01) |
| *A61K 33/20* | (2006.01) |
| *A61B 18/18* | (2006.01) |
| *A61F 13/06* | (2006.01) |
| *A61F 13/10* | (2006.01) |

(52) U.S. Cl.
CPC ............ *A61N 1/0428* (2013.01); *A61B 18/18* (2013.01); *A61K 31/02* (2013.01); *A61K 33/04* (2013.01); *A61K 33/20* (2013.01); *A61N 1/44* (2013.01); *A61F 13/068* (2013.01); *A61F 13/105* (2013.01)

(58) Field of Classification Search
None
See application file for complete search history.

(56) References Cited

U.S. PATENT DOCUMENTS

| | | |
|---|---|---|
| 7,048,913 B2 | 5/2006 | Hexamer |
| 7,825,104 B2 | 11/2010 | Freeman et al. |
| 2008/0255498 A1 | 10/2008 | Houle |
| 2012/0039796 A1 | 2/2012 | Markou |
| 2014/0200506 A1 | 7/2014 | Zemel |
| 2016/0166607 A1* | 6/2016 | Roe ........................ A61K 31/02 424/600 |

FOREIGN PATENT DOCUMENTS

WO    WO-2011115585 A1 *    9/2011    .......... A61K 31/4164

* cited by examiner

*Primary Examiner* — Dennis J Parad

(57) ABSTRACT

A system and method includes delivery of a redox gas solution to treat onychomycosis, wherein the redox gas solution comprises a reactive species dissolved in a perfluorocarbon liquid, and wherein the perfluorocarbon liquid is dispensed onto a gas-permeable membrane and the perfluorocarbon liquid comprises of an anti-inflammatory in a perfluorocarbon liquid and wherein the reactive species may include, alone or in combination, one or more of reactive oxygen, reactive nitrogen, reactive chlorine, or reactive bromine species, and the perfluorocarbon liquid may include perfluorodecalin.

8 Claims, 17 Drawing Sheets

ONYCHOMYCOSIS TREATMENT SYSTEM AND METHOD

RELATED APPLICATIONS

This application is a continuation-in-part of, and is related to and claims priority from, pending U.S. patent application Ser. No. 15/464,761, filed Mar. 21, 2017, and pending U.S. patent application Ser. No. 14/963,552, filed Dec. 9, 2015, which is related to and claims priority from U.S. provisional patent application Ser. No. 62/089,945, filed Dec. 10, 2014, entitled Onychomycosis Treatment Apparatus and Method, each of which is hereby incorporated by reference herein for all purposes.

STATEMENT REGARDING FEDERALLY SPONSORED RESEARCH OR DEVELOPMENT

This invention was made with government support under NSF Award ID 1343994 and NIH Award ID 1R43GM112196-01 awarded by the National Science Foundation and the National Institute of Health. The government has certain rights in the invention.

FIELD OF THE DISCLOSURE

The invention in one aspect relates generally to a system and method for the treatment of tissue infected with onychomycosis.

BACKGROUND

Onychomycosis (also known as "dermatophytic onychomycosis," or"tinea unguium") is a fungal infection of the nail. It is the most common disease of the nails and constitutes about half of all nail abnormalities. This condition may affect toenails or fingernails, but toenail infections are particularly common. It occurs in about 10% of the adult population.

The most common symptom of a fungal nail infection is the nail becoming thickened and discolored. As the infection progresses the nail can become brittle, with pieces breaking off or coming away from the toe or finger completely. If left untreated, the skin can become inflamed and painful underneath and around the nail. There may also be white or yellow patches on the nail bed or scaly skin next to the nail, and an odor may result. Many times, the tissue surrounding the affected nail has inflammation and treatment of that tissue is also desirable. There is usually no pain or other bodily symptoms, unless the disease is severe. People with onychomycosis may experience significant psychosocial problems due to the appearance of the nail, particularly when fingers—which usually are always visible—rather than toenails are affected.

Dermatophytids are fungus-free skin lesions that sometimes form as a result of a fungus infection in another part of the body. This could take the form of a rash or itch in an area of the body that is not infected with the fungus. Dermatophytids can be thought of as an allergic reaction to the fungus.

The causative pathogens of onychomycosis include dermatophytes, *Candida*, and non-dermatophytic molds. Dermatophytes are the fungi most commonly responsible for onychomycosis in the temperate western countries; while *Candida* and nondermatophytic molds are more frequently involved in the tropics and subtropics with a hot and humid climate.

*Trichophyton rubrum* is the most common dermatophyte involved in onychomycosis. Other dermatophytes that may be involved are *T. interdigitale, Epidermophyton floccosum, T. violaceum, Microsporum gypseum, T. tonsurans*, and *T. soudanense*. A common outdated name that may still be reported by is *Trichophyton mentagrophytes* for *T. interdigitale*. The name *T. mentagrophytes* is now restricted to the agent of favus skin infection of the mouse; though this fungus may be transmitted from mice and their danders to humans, it generally infects skin and not nails.

Other causative pathogens include *Candida* and nondermatophytic molds, members of the mold generation *Scytalidium* (name recently changed to *Neoscytalidium*), *Scopulariopsis*, and *Aspergillus*. *Candida* mainly causes fingernail onychomycosis in people whose hands are often submerged in water. *Scytalidium* mainly affects people in the tropics, though it persists if they later move to areas of temperate climate.

All causative pathogens are susceptible to certain toxic gasses, such as ozone, oxides of nitrogen, and similar reactive materials. It is understood that fluid and solid materials may also have similar beneficial anti-pathogenic properties. However, there are a number of problems associated with the use of such anti-pathogenic substances to treat onychomycosis. The nail bed itself can act as a barrier to curative gasses and beneficial anti-pathogenic substances. Additionally, the curative gasses can cause inflammation to the tissue surrounding the affected nail and the inflammation is a negative side effect of the treatment. Thus, there remains a need for a system and method for the treatment of onychomycosis that permits substances to traverse, surround and/or enter the nail bed and similar physiological structures for a beneficial effect while mitigating the effect of inflammation to the surrounding tissue.

There also remains an unmet medical need for a topical treatment device and treatment method for onychomycosis that is effective, requiring short treatment times and without the undesirable side effects of the prior art. Many chemical compounds exhibit antifungal (fungistatic or fungicidal) properties, and can be incorporated into creams, lotions, gels, solutions and the like. However, antifungal compounds applied topically (i.e., directly to the nail) do not adequately and consistently penetrate the nail bed to kill the fungus at its source, and thus are not consistently effective.

There also remains an unmet medical need for a topical treatment device and treatment method for onychomycosis that is effective, requiring short treatment times, provides a reduction in inflammation in the surrounding skin and without the undesirable side effects of the prior art. Many chemical compounds exhibit antifungal (fungistatic or fungicidal) properties, and can be incorporated into creams, lotions, gels, solutions and the like. However, antifungal compounds applied topically (i.e., directly to the nail) do not adequately and consistently penetrate the nail bed to kill the fungus at its source, and thus are not consistently effective and they irritate the surrounding skin so a means to minimize the effect of inflammation in the surrounding skin is needed.

Thus, an additional or improved apparatus and method for treating onychomycosis that is effective and reduces skin inflammation of the surrounding tissue or skin is desirable.

SUMMARY

The present disclosure provides a system and method that includes delivery of a redox gas solution to treat onychomycosis, wherein the redox gas solution comprises a reactive species dissolved in a perfluorocarbon liquid. The perfluorocarbon liquid having an anti-inflammatory agent in suspension in the perfluorocarbon liquid.

In one exemplary embodiment, the reactive species may include, alone or in combination, one or more of reactive oxygen, reactive nitrogen, reactive chlorine, or reactive bromine species. The perfluorocarbon liquid may include perfluorodecalin. The perfluorocarbon liquid preferable has an anti-inflammatory agent in it to reduce inflammation in tissue from the infection and the exposure to the curative gasses.

In one exemplary embodiment, a system is provided that may include a housing with a chamber disposed therein. The chamber may include an opening through which a foot or hand to be treated may be at least partially inserted. One or more reactive species generators may be disposed within the chamber. In one embodiment, the toes of the inserted foot or nails of the hand may be positioned a desired distance from the one or more reactive species generators. A disposable tray may be used to help prevent contact between the foot or hand and the sides (i.e., bottom, walls) of the housing chamber. In one embodiment, the disposable tray may include a curtain that closes the opening about the inserted foot or hand, e.g., to help prevent the escape of reactive species through the opening. During treatment, the generators provide for a desired period of time reactive species to the chamber including the inserted foot or hand.

In one exemplary embodiment, the perfluorocarbon liquid having an anti-inflammatory agent in suspension in the perfluorocarbon liquid. The perfluorocarbon liquid may include perfluorodecalin with anti-inflammatory agent suspended in the liquid. The anti-inflammatory agent can be added to the perfluorocarbon liquid either individually or in combination can be selected from the group including aspirin, Acetylsalicylic acid, salicylic acid, celecoxib (Celebrex), diclofenac (Cambia, Cataflam, Voltaren-XR, Zipsor, Zorvolex), diflunisal (Dolobid—discontinued brand), etodolac (Lodine), ibuprofen (Motrin, Advil), Ketorolac tromethamine, indomethacin (Indocin) and drugs that meet the definition of NSAIDs—nonsteroidal anti-inflammatory drugs.

In one exemplary embodiment, the perfluorocarbon liquid having an anti-inflammatory agent in suspension in the perfluorocarbon liquid is pre-loaded into a toe cot or elastic sleeve. These sleeves are placed onto the treatment subjects infected toes by the doctor or patient to cover the infected toenails before the foot is slipped into the plasma treatment chamber.

In another exemplary embodiment, the chamber of the treatment instrument may include a disposable transfer medium gas-permeable membrane installed on a dispensing reel and a take-up reel and a syringe having anti-inflammatory perfluorocarbon solution. The membrane would be positioned between one or more reactive species generators and the toes of the inserted foot or nails of the hand. In one embodiment, the toes of the inserted foot or nails of the hand may be positioned so that they touched the membrane that is imbibed or saturated with anti-inflammatory perfluorocarbon. Before start of treatment, the syringe would disperse anti-inflammatory perfluorocarbon solution onto the membrane so that the solution imbibed or saturated into the membrane such that it coated the membrane and nails. During treatment, the generators provide for a desired period of time reactive species to the chamber including the inserted foot or hand.

Other benefits and advantages of the present disclosure will be appreciated from the following detailed description.

DESCRIPTION OF THE DRAWINGS

Exemplary embodiments of a system and method are shown in the accompanying drawings.

DETAILED DESCRIPTION

An anti-inflammatory agent is defined within this invention to mean aspirin, Acetylsalicylic acid, salicylic acid, celecoxib (Celebrex), diclofenac (Cambia, Cataflam, Voltaren-XR, Zipsor, Zorvolex), diflunisal (Dolobid—discontinued brand), etodolac (Lodine—discontinued brand), ibuprofen (Motrin, Advil), Ketorolac tromethamine, indomethacin (Indocin) and drugs that meet the definition of NSAIDs—nonsteroidal anti-inflammatory drugs.

Embodiments of the invention and various alternatives are described. Those skilled in the art will recognize, given the teachings herein, that numerous alternatives and equivalents exist which do not depart from the invention. It is therefore intended that the invention not be limited by the description set forth herein or below.

One or more specific embodiments of the system and method will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Further, for clarity and convenience only, and without limitation, the disclosure (including the drawings) sets forth exemplary representations of only certain aspects of events and/or circumstances related to this disclosure. Those skilled in the art will recognize, given the teachings herein, additional such aspects, events and/or circumstances related to this disclosure, e.g., additional elements of the devices described; events occurring related to onychomycosis treatment; etc. Such aspects related to this disclosure do not depart from the invention, and it is therefore intended that the invention not be limited by the certain aspects set forth of the events and circumstances related to this disclosure.

Figure 1:
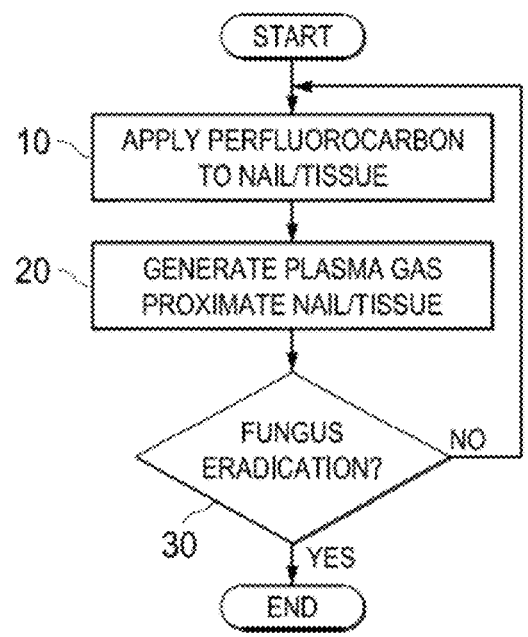
FIG. 1 is an illustration by flowchart of an exemplary method in accordance with the disclosure.

Turning now to the drawings, the figures show an exemplary treatment system and method. As described in FIG. 1, the system provides delivery of a redox gas solution to treat onychomycosis, wherein the redox gas solution comprises a reactive species dissolved in a perfluorocarbon liquid. The perfluorocarbon liquid is applied at step 10 to the nail/tissue. Then, at step 20, a plasma gas is generated proximate the nail/tissue. The plasma gas forms reactive species that dissolve in the perfluorocarbon liquid to form a redox gas solution. The process may repeat or continue until sufficient redox gas solution is produced to eradicate nail/tissue fungus. See step 30.

In one exemplary embodiment, the reactive species may include, alone or in combination, one or more of reactive oxygen, reactive nitrogen, reactive chlorine, or reactive bromine species. The reactive species may be formed through use of a non-thermal plasma device, or otherwise be provided.

Figure 2:
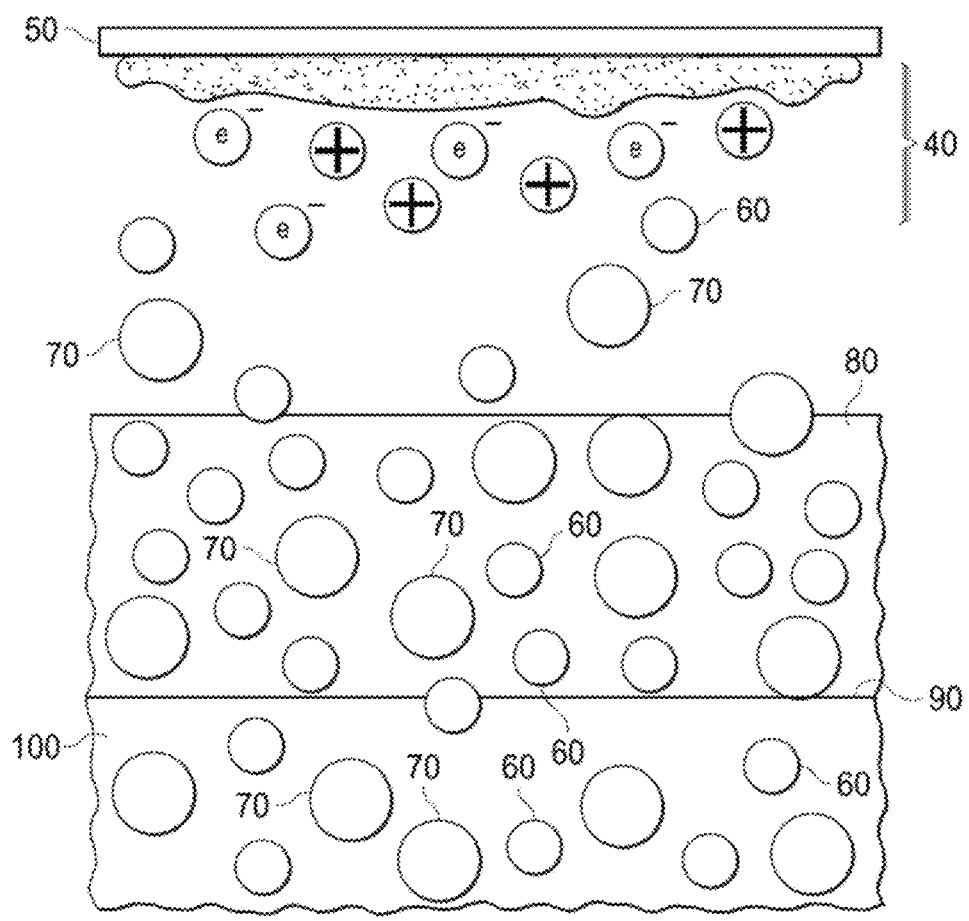
FIG. 2 is a cross-sectional view of a portion of an exemplary system in accordance with the disclosure.
Figure 3A:
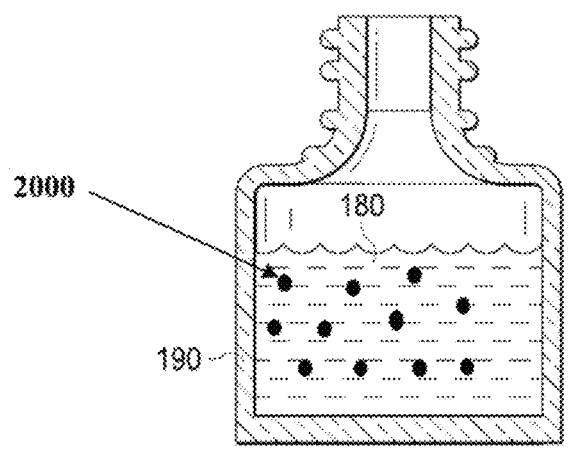
FIG. 3A is a cross-sectional view of a container including an exemplary perfluorocarbon liquid in accordance with the disclosure.
Figure 3B:
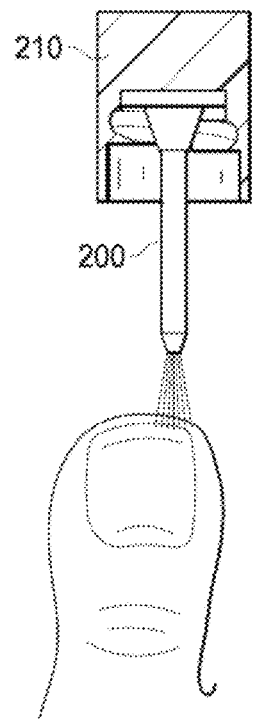
FIG. 3B is a cross-sectional view of a cap for the container shown in FIG. 3A, the cap including an applicator for providing perfluorocarbon liquid to a nail/tissue.
Figure 3C:
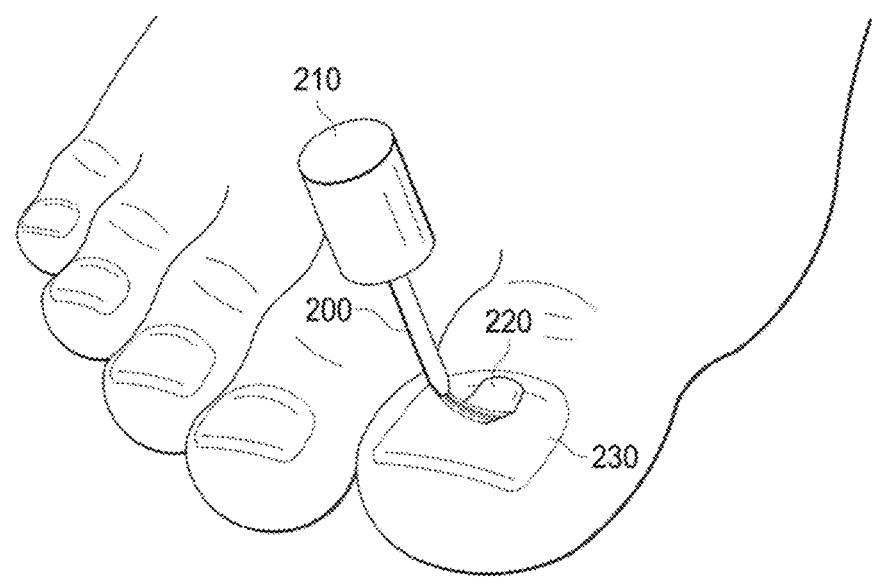
FIG. 3C is a perspective view of an exemplary application of perfluorocarbon liquid to nail/tissue using the applicator shown in FIG. 3B.

As shown in FIG. 2, a plasma 40 may be formed proximate a ground electrode 50. The plasma forms reactive species 60, 70. The reactive species 60, 70 dissolve in a perfluorocarbon liquid 80 applied to the surface 90 of nail/tissue 100. The redox gas solution including reactive species 60, 70 diffuses into the nail/tissue bed to eradicate fungus located therein. As shown in FIG. 2, the plasma generating device includes a ground electrode 50. In addition, the device generates a sufficiently high voltage signal applied between two electrodes, one of which is the ground electrode 50, where at least one of the electrodes is insulated for plasma generation (not shown for clarity in FIG. 2).

Perfluorocarbon Liquids (PFCs)/Other Facilitators

The perfluorocarbon liquid may include perfluorodecalin. Perfluorodecalin and other suitable perfluorocarbon liquids have desirable wetting, gas absorption and diffusion properties.

The terms suspension, mixture and solution as used herein are used interchangeably to mean a mixture of anti-inflammatory agent and perfluorocarbon liquid.

Perfluorocarbons (PFCs), fluorocarbons, or perfluorochemicals (terms which may be used interchangeably) liquids are formally derived from liquid hydrocarbons by replacing all the hydrogen atoms with fluorine atoms. This class of chemical compounds is characterized by its property to be extremely inert—chemically, biologically, and physiologically—due to the remarkable stability of the C—F bonds. The C—F bond is the strongest bond encountered in organic chemistry, and its strength is further increased when several fluorine atoms are present on the same carbon atom. The presence of fluorine even reinforces the strength of the C—C bonds.

PFC liquids generally are clear, colorless, odorless, electrically non-conducting, and nonflammable. They are approximately twice as dense as water, and generally are capable of dissolving large amounts of physiologically important gases. For their gas uptake function, PFCs act only as a carrier of the gasses and do not react with the gas or produce the gases. PFCs are generally very chemically stable compounds that are not metabolized in body tissues. They are physiologically inert as there is no enzyme system capable of modifying liquid PFCs, neither metabolically nor catabolically. Liquid PFCs are both hydrophobic and lipophobic, i.e., they are immiscible both with water and lipophilic liquids and generally form emulsions with them. Therefore, to mix the anti-inflammatory agent into the PFC liquids requires that significant energy be applied to the mixture similar to that found in U.S. Pat. No. 9,210,806, and is hereby incorporated by reference herein for all purposes. This mixture is made by taking 10 mg of Sigma A5376 Acetylsalicylic acid and placing it in a 300-ml suitable glass container such as a beaker. Then add 200 ml of perfluorodecalin but any perfluorocarbon liquid described can be used. Then place the sonicator tip of a Branson Sonifier 450 so that it extends to approximately 2 mm from the bottom of the beaker. Set the power supply for controls accordingly to 20% Duty Cycle, Output control to 6 and timer to 8. Cover the beaker with a piece of plastic film such as Parafilm® M Sealing Film to prevent splatter or contamination and sonicate for 20 minutes. The anti-inflammatory agent is adequately mixed when the anti-inflammatory agent is completely suspended in the perfluorocarbon liquid when none of the powder is resting on the bottom of the beaker. The beaker can be replaced by any suitable glass container.

PFCs are used in a variety of industries. They were first synthesized in the 1920s and developed for industry in the 1940s. PFCs are currently being used in retinal detachment surgery, liquid ventilation therapy for the lungs, as a blood substitute and as ultrasound and radiological imaging agents. They are used in both cosmetics and paints to facilitate easier product spreading and in textile manufacturing as a fabric protector.

The term "perfluorocarbon liquid" or "PFC liquid" as used herein may include organic compounds in which all (or essentially all) of the hydrogen atoms are replaced with fluorine atoms. Representative perfluorinated liquids include cyclic and non-cyclic perfluoroalkanes, cyclic and non-cyclic perfluoroamines, cyclic and noncyclic perfluoroethers, cyclic and non-cyclic perfluoroaminoethers, and any mixtures thereof.

The term "membrane" is defined as a gas permeable membrane composition that comprises at least one material selected from ceramics, polymers, woven substrates, non-woven substrates, polyamide, polyester, polyurethane, fluorocarbon polymers, polyethylene, polypropylene, polyvinyl alcohol, polystyrene, vinyl, plastics, metals, alloys, minerals, non-metallic minerals, wood, fibers, cloth, glass, and hydrogels.

Specific examples of perfluorinated liquids include the following: perfluoropentane, perfluorohexane, perfluoroheptane, perfluorooctane, perfluorodecalin, perfluoromethylcyclohexane, perfluorotributyl amine, perfluorotriamyl amine, perfluoro-N-methylmoφholine, perfluoro-Nethylmoφholine, perfluoroisopropyl moφholine, perfluoro-N-methyl pyrrolidine, perfluoro-1,2 is(trifluoromethyl)hexafluorocyclobutane, perfluoro-2-butyltetrahydrofuran, perfluorotriethylamine, perfluorodibutyl ether, and mixtures of these and other perfluorinated liquids.

Perfluorocarbons in general improve gas exchange and are a desirable medium to carry redox gases. PFC at one atmosphere of pressure can carry 20 times more oxygen than saline will hold. PFCs are low viscosity surfactants that may lower the surface tension on the nail, so the PFC may spread uniformly and quickly over the nail structure. The low surface tension contributes to improved wetting of the surfaces. The surface tensions of PFC's are generally less than 20 dynes/cm and usually between 10 to 20 dynes/cm when measured at 25° C. When used in lung injury for ARDS patients, surface tension in the lung is noted to be 67 to 75 dynes/cm. In a lung with PFC, the surface tension is only 18 dynes/cm, which helps prevent alveolar collapse and reduces alveolar opening pressures.

PFCs may displace water and circulate to those areas where gas exchange is diminished. PFCs also may wash out debris if the debris is lighter than the PFC used. PFCs are not taken up by the body and do not break down into toxic metabolites.

Perfluorocarbon liquids may be compounds containing a high level of carbon-bound fluorine that are liquid at or below 106° F. at atmospheric pressure. These fluorinated fluids may be capable of dissolving a substantial amount of a redox gas at operating conditions, typically, in a temperature range from about 0° C. to about 50° C. The perfluorocarbon liquid may be converted in whole or in part to a redox gas solution before topical application by dissolving the reactive gaseous species into perfluorocarbon liquid at the manufacturing facility and delivering the topical composition to the customer in a usable form such that the customer can apply the solution to the infected area as a treatment. In one exemplary embodiment, PFC fluids may dissolve at least 500 mL of gaseous chlorine per 100 mL of fluid at 1 atm and 25° C. In another exemplary embodiment, the PFC fluids may dissolve at least 1200 mL of gaseous chlorine at 1 atm and 25° C. The oxidizing gas solutions used in the described methods may be saturated with a desired oxidizing gas. In another example, the concentration of ozone in the PFC may be greater than 1 ppm but less than 500 ppm. Fluorinert™ Fluids, product bulletin 98-0211-8301-1 (65.05)R, issued 5/95, available from 3M Co., St. Paul, Minn., provides the solubility of many oxidizing gases in Fluorinert™ Electronic Fluids.

Other perfluorocarbons that may be used include, by way of example, perfluorocarbons such as fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotributylamines, fluorotriethylamines, perfluorohexanes, perfluoropentanes, perfluorobutanes, perfluoropropanes, sulfur hexafluoride, Methylperfluorobutylether (GransilSiW 7100) or Perfluoro (tert-butylcyclohexane). Also, mixtures of perfluorocarbons could also be utilized in this invention that combine different perfluorocarbons and perfluorocarbon compositions such as PFC emulsions or PFC gels.

Other liquids may fulfill the mechanism of penetration enhancer/gas carrier and could concentrate the antifungal species from the plasma. In addition to PFCs, alternative molecules that both concentrate and promote gas exchange may be used and include, but are not limited to, neuroglobin, apomyoglobin, hemoglobin, myoglobin, and synthetic blood or blood substitutes such as respirocytes.

To minimize inflammation around the skin or tissue surrounding the infection an anti-inflammatory agent can be mixed with the perfluorocarbon. The anti-inflammatory agent is helpful for both inflammations due to the proximal infection or from the effect of exposure to the curative gasses. The anti-inflammatory agent can be selected from any or a combination of the following aspirin, Acetylsalicylic acid, salicylic acid, celecoxib (Celebrex), diclofenac (Cambia, Cataflam, Voltaren-XR, Zipsor, Zorvolex), diflunisal (Dolobid—discontinued brand), etodolac (Lodine—discontinued brand), ibuprofen (Motrin, Advil), indomethacin (Indocin, Ketorolac tromethamine and drugs that meet the definition of NSAIDs—nonsteroidal anti-inflammatory drugs. The anti-inflammatory agent has to be mixed by high energy sonification to form a suspension with the perfluorocarbon liquid.

In another exemplary embodiment, the perfluorocarbon or other liquid may include a co-solvent to improve as desired specific physical properties of the fluid. A semifluorinated alkane (SFA) that has a non-fluorinated hydrocarbon segment may be added to a PFC liquid. In another exemplary embodiment, the liquid composition may comprise the combination of more than one PFC and/or more than one SFA. It may be useful to combine PFCs and SFAs, for example, to achieve a particular desired target property, such as a certain density, viscosity, lipophilicity or soluble capacity for a particular active ingredient such as a dye. The SFA may be essentially non-reactive with the redox gas. The SFA also may not reduce the solubility of the redox gas in the PFC. In one exemplary embodiment, one or more useful SFAs may be selected from a group of SFAs including $F_4H_5$, $F_4H_6$, $F_4H_8$, $F_6H_6$ and $F_6H_8$. Additionally, the SFA can include an anti-inflammatory agent which has to be mixed by high energy sonification to form a suspension with the liquid.

Redox Gas Solutions

In one exemplary embodiment, the perfluorocarbon liquid absorbs anti-pathogenic substances generated by a plasma-generating device. See, e.g., FIG. 2. In one exemplary aspect, onychomycosis treatment is enhanced using a solution containing gaseous reactive oxygen or reactive nitrogen or reactive chlorine/bromine species that are dissolved in a perfluorocarbon liquid.

For convenience only, and without limitation, a solution containing gaseous reactive oxygen or reactive nitrogen or reactive chlorine/bromine species dissolved in a perfluorocarbon liquid shall be referred to herein as a "redox gas solution."

In accordance with another exemplary embodiment, an onychomycosis treatment system and method includes a topical composition to overcome one or more disadvantages of current topical fungal treatments. In one aspect, the topical composition may include a redox gas solution.

In another aspect, a further exemplary embodiment provides a method of treating fungal infections like onychomycosis comprising contacting a skin or nail surface with a perfluorocarbon liquid, and converting at least a portion of the perfluorocarbon liquid into a redox gas solution. In another aspect, such method includes the step of dissolving a redox gas in a perfluorocarbon liquid proximate the site of a fungal infection like onychomycosis to be treated. In another exemplary embodiment, the redox gas is formed during a non-thermal plasma treatment step.

In accordance with another exemplary embodiment, first and second treatment vectors for a fungal infection like onychomycosis are provided, wherein the first vector includes a redox gas formed as a result of a non-thermal plasma treatment step, and the second vector includes a redox gas solution.

Plasma-Generating Devices

In accordance with one exemplary embodiment, a plasma-generating device may create antimicrobial plasma species proximate a nail or skin area to be treated.

As used herein, the term "antimicrobial" means tending to destroy microbes, prevent their development, or inhibit their pathogenic action, and includes reference to, without limitation, antibacterial and antifungal properties.

Plasma is a gas-like phase of matter that typically contains many more reactive chemistry species than gas. A plasma-generating device turns electrical energy and a preselected gas (typically air, argon or helium) into electric fields, energetic electrons and favorable chemistry for antimicrobial therapy.

There are multiple technologies that have been used for plasma-generating devices at atmospheric pressure and temperatures. Non-thermal plasma gas at atmospheric pressure have been generated by microwave-induced plasma systems, dielectric barrier discharge (DBD), corona discharge, gliding arc discharge, and atmospheric pressure plasma jet. U.S. Pat. No. 7,572,998 is hereby expressly incorporated by reference herein in its entirety for all purposes. The '998 patent describes some representative, but not exclusive, plasma generators that may be useful.

Figure 4:
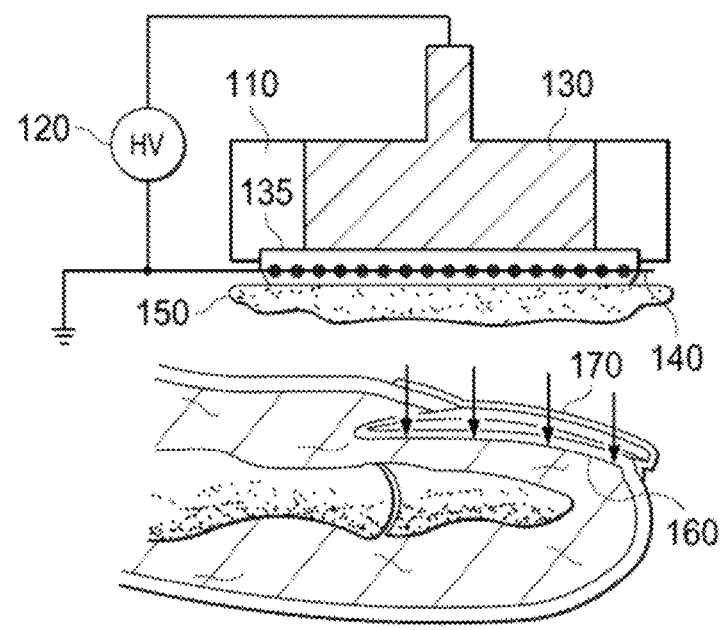
FIG. 4 is a partial schematic view of an exemplary plasma generating device proximate nail/tissue to which a perfluorocarbon liquid has been applied in accordance with the disclosure.

As shown in FIG. 4, the plasma-generating device 110 is electrically connected to both a power supply 120 and electrical control circuit to control both the duration and intensity of the plasma gas effluent 160. The electrical system may generate a high-voltage alternating current, typically between 2 to 20 kV at a frequency between 1 to 60 kHz. The power consumption may range from 0.05 W to 10.0 W. The high voltage electrode 130 may include a cylindrical copper block covered by a thin quartz plate 135 (e.g., approximately 1 mm in thickness). A stainless-steel woven wire mesh may be positioned next to the quartz plate 135 and used as the ground electrode 140. A wire diameter of 0.5 mm and mesh density of 8×8 meshes per cm$^2$, for example, may be used.

A variation of the dielectric barrier discharge (DBD), the surface micro-discharge (SMD) may prove advantageous as the plasma-generating device in applications for igniting a stable plasma at ambient conditions. A SMD is a configuration of a DBD where the high voltage electrode is separated from a grounded electrode by a dielectric layer. The term dielectric barrier discharges may be used because a high electric field is generated through an electrical insulator (e.g., glass) to create a plasma. In a SMD, the charged particles may be confined to a plasma generation region around the grounded metal electrode. A SMD may be a desirable source of reactive chemical species for several reasons: the treated body part is electrically isolated from high-voltage electrode due to ground electrode; the discharges are non-thermal, increasing adjacent gas temperature slightly, e.g., by only a few degrees; devices can be scaled simply, e.g., by changing electrode size and input power; and the discharges may operate in ambient air, e.g., without requiring a noble gas mixture. SMD devices have been further described in a series of articles by Graves et al. and Morfill et al.

Multiple reactive oxygen species (ROS) and reactive nitrogen species (RNS) may be generated in a non-thermal plasma. The active content of the plasma effluent at the treatment surface may include, for example, singlet oxygen (1O2), hydroxide (OH), hydrogen peroxide ($H_2O_2$), ozone ($O_3$), nitrous oxide ($N_2O$), nitrogen dioxide ($NO_2$) and other excited molecules of air constituents that includes other reactive nitrogen and reactive oxygen species such as $HNO_2$, $NO_3$, $HNO_3$ and $N_2O_5$. Side reactions with these chemistries also may generate beneficial liquids and solids as the nail keratin and water in the nail can maintain antifungal properties long after the treatment is complete. Charged particles, electric fields and UV light also may be generated by plasma. The ionized gases generally last for very short periods of time (e.g., less than a second), but free radicals and reactive oxygen and nitrogen species that are electrically neutral may last long enough to be effective—perhaps up to many meters away from the source—in destroying fungus, bacteria and their spores. These free radicals denature critical lipid, protein and nucleic acid contents of the microbes, ultimately causing cell death. Research has demonstrated the effectiveness of plasma gas as well as nitrogen and oxygen free radicals such as ozone or hydrogen peroxide vapor or a combination of these in causing retarded fungal growth and fungal death. The byproduct of the plasma process is water ($H_2O$) and carbon dioxide ($CO_2$). Kogelschatz and co-workers have performed early studies on the discharge characteristics and chemistry of air DBDs. More recently Y. Sakiyama et al. created a plasma chemistry model of a SMD device to determine the dynamics of the reactive neutral species it produces.

The non-thermal plasma gas effluent may be directed to a treatment site in two ways: direct mode or indirect mode. Direct mode (see FIG. 4) puts the treatment area within the visible plasma region discharge or plume, which may be between about 0.0 mm and about 5.0 mm for most devices. In direct mode, UV light, some charged particles and electric fields, in addition to reactive neutral species, may directly reach the treatment surface 160, to which a perfluorocarbon 170 may be applied. Indirect mode may have the treatment surface between about 5.0 mm and about 1.0 meter away. Thus, charged particles and electric field may have dissipated or decayed and may not reach the treatment surface. The indirect mode may benefit from a gas delivery system, wherein the plasma gas effluent may be directed to the treatment surface with tubing, inline fans, connectors, ports, etc. for input, delivery and output of antimicrobial agent to the treatment surface. That is, simple diffusion or forced air flow may promote delivery of reactive species to the nail bed, where the non-thermal plasma effluent or gas composition acts as an antimicrobial agent.

Treatment may occur for a predetermined or desired period of time. The antimicrobial agent may be applied for a sufficient time to achieve an effective killing of all or a portion of the fungus within the nail structure. For example, a sufficient time for application may be a time from about 10 seconds to about 4 hours. In one exemplary embodiment, antimicrobial agent may be applied for a time from about 1 minute to about 15 minutes. In yet another exemplary embodiment, antimicrobial agent may be applied for a time from about 5 minutes to about 20 minutes. In a further exemplary embodiment, antimicrobial agent may be applied for a time from about 30 minutes to about 1 hour. In other exemplary embodiments, the application of antimicrobial agent may be cyclical in nature, wherein an electrical control circuit cycles the device on and off, e.g., for a predetermined period of time (for example a 50% duty cycle (1 minute on/1 minute off) for a 30 minute to 1 hour treatment period).

Gaseous Species

Other reactive gases not created by a non-thermal plasma generator may be useful in making redox gas solutions. Such other reactive gases may include any gas capable of directly causing or actively triggering a reaction that eradicates pathogens within or on the surface of a material (e.g., skin or nail) where the gas is also readily soluble in a perfluorocarbon fluid. Such gases include, for example, methanethiol, bromine, chlorine, nitric oxide, ozone, chlorine dioxide, and/or sulfur dioxide. Reactive oxygen and reactive nitrogen species play a central role in oxidation-reduction biochemistry (also called redox biology) and are active in the immune response of both animals and plants. The reactive oxygen/nitrogen/chlorine/bromine or sulfur species listed in Table 1 may be useful in making redox gas solutions.

TABLE 1

List of various reactive oxygen, nitrogen, halogen and sulfur species [10, 22, 23].

| Radical | Non-radical |
| --- | --- |
| Reactive oxygen species (ROS) | |
| Superoxide, $O_2^-$ | $H_2O_2$ |
| Hydroxyl, OH | Ozone, $O_3$ |
| Hydroperoxyl, $HO_2$ | Singlet oxygen ($O_2$ 1 Dg) |
| Carbonate, $CO_3^-$ | Hypobromous acid, HOBr |
| Peroxyl, $RO_2$ | Hypochlorous acid, HOCl |
| Alkoxyl, RO | |
| Carbon dioxide radical $CO_2^-$ | Hypoiodous acid, HOI |
| Singlet ($^1O_2$) | Organic peroxides, ROOH |
| | Peroxynitrite, ONOO— |
| | Peroxynitrate, $O_2$NOO— |
| | Peroxynitrous acid, ONOOH |
| | Peroxomonocarbonate, $HOOCO_2^-$ |
| | Carbon monoxide, CO |
| Reactive chlorine/bromine species | |
| Atomic chlorine, Cl | Chloramines |
| Atomic Bromine, Br | Chlorine gas, $Cl_2$ |
| | Bromine gas, $Br_2$ |
| | Bromine chloride, BrCl |
| | Chlorine dioxide, $ClO_2$ |
| Reactive nitrogen species (RNS) | |
| Nitric oxide, NO | Nitrous acid, $HNO_2$ |
| Nitrogen dioxide, $NO_2$ | Nitrosyl cation, $NO^+$ |

TABLE 1-continued

List of various reactive oxygen, nitrogen, halogen and sulfur species [10, 22, 23].

| Radical | Non-radical |
| --- | --- |
| Nitrate radical, $NO_3$ | Nitroxyl anion, $NO^-$ |
| | Dinitrogen trioxide, $N_2O_3$ |
| | Dinitrogen tetroxide, $N_2O_4$ |
| | Dinitrogen pentoxide, $N_2O_5$ |
| | Alkyl peroxynitrites, ROONO |
| | Alkyl peroxynitrates, $RO_2ONO$ |
| | Nitryl chloride, $NO_2Cl$ |
| | Peroxyacetyl nitrate, $CH_3C(O)OONO_2$ |
| Reactive sulfur species | |
| Thiyl radical S. | Hydrogen sulfide, $H_2S$ |
| | Disulfide, RSSR |
| | Disulfied-S-monoxide, RS(O)SR |
| | Disulfide-S-dixide, RS(O)2SR |
| | Sulfenic acid, RSOH |
| | Thiol/sulfide, RSR |

Graves RONS Review Paper 2012

Redox gases can be purchased in their gaseous form but, due to their relatively high vapor pressure, require expensive sealed and pressurized tanks for storage. To provide handling convenience and cost-effectiveness, redox reagents are often created in an aqueous solution such as hypochlorous acid (generated from sodium hypochlorite), hydrogen peroxide, or nitric acid. These aqueous solutions are, however, less reactive than their gaseous counterparts, often requiring elevated temperatures and significant time to complete the redox reaction in situ.

A redox gas may be added to a perfluorocarbon liquid, which has already been mixed with the proper amount of anti-inflammatory agent, by any conventional technique (e.g., sparging or gas injection or simple diffusion) to create a redox gas solution. A typical sintered sparger can be purchased from Mott corporation http://mottcorp.com. Such redox gas solutions provide a means for delivering a stable solution of an oxidation or reduction gas in its most active, non-hydrolyzed state that also allows handling convenience and cost-effectiveness.

Effective treatment of fungal nail infection may come from combining a redox gas with a perfluorocarbon and anti-inflammatory agent liquid, then applying the redox gas solution topically, so that it penetrates the nail plate and inactivates pathogens residing in the nail bed. The anti-inflammatory agent is incorporated into the perfluorocarbon liquid to mitigate the inflammation due to exposure of the tissue to the local infection or the gas.

A method for treating nail fungus may comprise the steps of: preparing a redox gas solution including an anti-inflammatory agent and applying the redox gas solution to the infected nails. An applicator may be used to coat the infected nail.

As shown in FIGS. 3A-3C and FIG. 13 in one exemplary embodiment, a redox gas solution 180 may include chlorine dioxide gas dissolved in perfluorodecalin and anti-inflammatory agent 2000 to saturation and may be provided in a container 190 as a topical treatment for onychomycosis. The solution may have a minimum of 80 ppm chlorine dioxide as the treating agent. Treating an infected nail with the solution comprises using an applicator 200 (for example coupled to the cap 210 of container 190) to spread a coating 220 on and around the nail 230. In one embodiment, such application includes a series of successive treatments to improve the aesthetic appearance of the nail, destroy the fungal infection and promote healthy nail growth. In another embodiment, the solution may be applied once a day for a minimum of sixty days to inactivate the fungus. In another embodiment, the solution may be applied once a week to prevent fungus or fungal spores from reinfecting the nail matrix.

A redox gas solution alternately may be generated at the skin or nail site by applying a perfluorocarbon liquid topically to the treatment area then treating the site with a redox gas, such as a gas created by a plasma-generating device. See FIGS. 2 and 4.

As an example, a perfluorocarbon liquid and anti-inflammatory agent mixture may be administered immediately prior to treatment with a non-thermal plasma device in an amount sufficient to enhance the permeation of antifungal gas through and around the nail. The non-thermal plasma device allows the in-situ generation of gaseous reactive oxygen species and reactive nitrogen species that have antifungal properties. The anti-inflammatory agent mixed with the perfluorocarbon liquid can be selected from any or a combination of the following aspirin, Acetylsalicylic acid, salicylic acid, celecoxib (Celebrex), diclofenac (Cambia, Cataflam, Voltaren-XR, Zipsor, Zorvolex), diflunisal (Dolobid—discontinued brand), etodolac (Lodine—discontinued brand), ibuprofen (Motrin, Advil), Ketorolac tromethamine, indomethacin (Indocin) and drugs that meet the definition of NSAIDs—nonsteroidal anti-inflammatory drugs.

Figure 13:
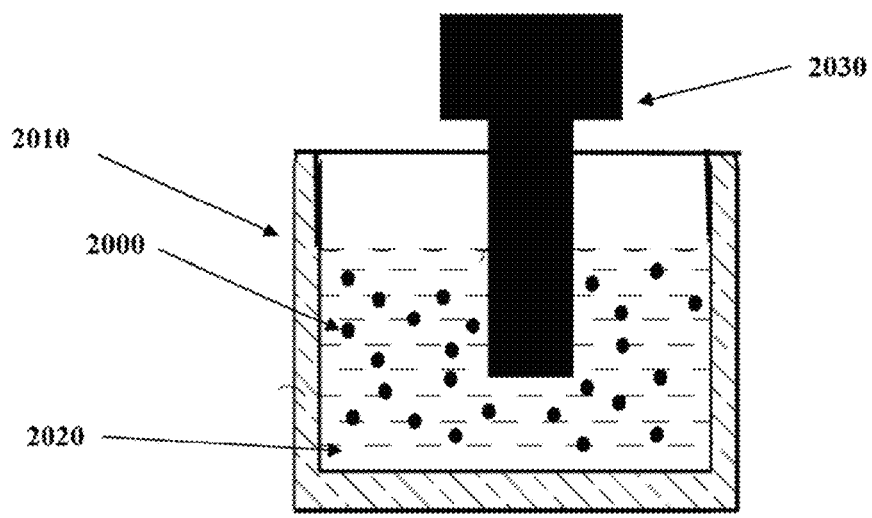
FIG. 13 is a cross-sectional view of a container including an exemplary perfluorocarbon liquid in accordance with the disclosure with an anti-inflammatory agent suspended in the liquid.
Figure 14:
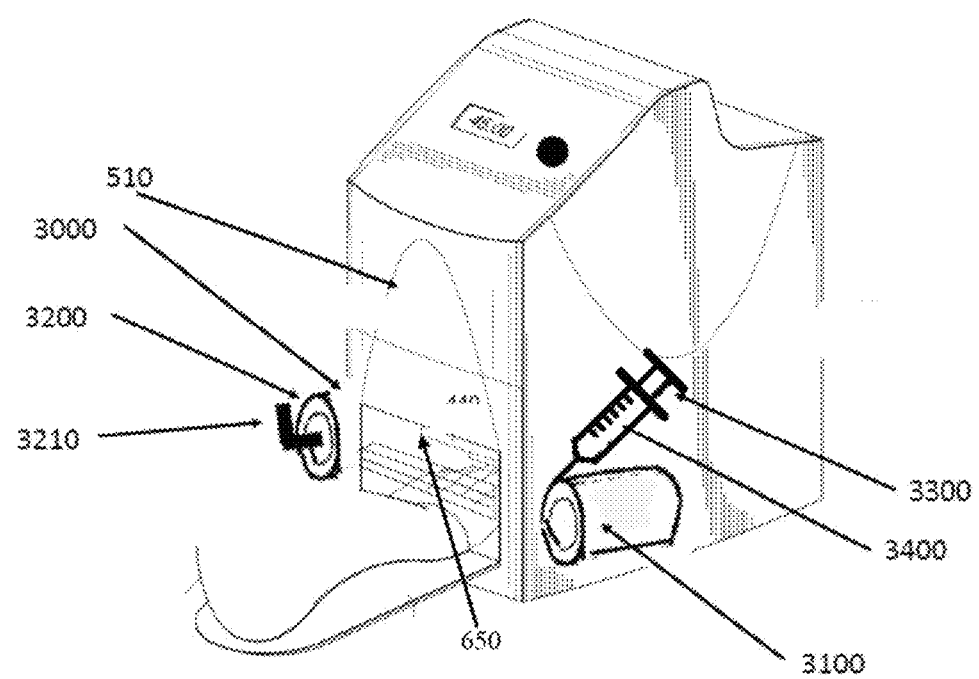
FIG. 14 is a perspective view of the treatment instrument with a disposable transfer medium gas-permeable membrane installed on a dispensing reel and a take-up reel and a syringe having anti-inflammatory perfluorocarbon solution.
Figure 15A:
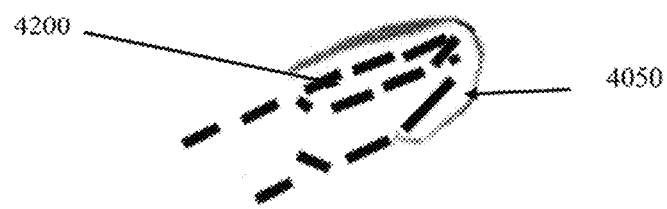
FIG. 15A is a perspective view a toe with a toe cot made from a disposable transfer medium gas-permeable membrane.
Figure 15B:
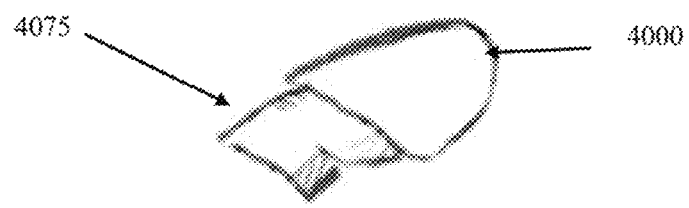
FIG. 15B is a perspective view a toe with a toe cot made from a disposable transfer medium gas-permeable membrane showing the toe in dotted lines.
Figure 15C:
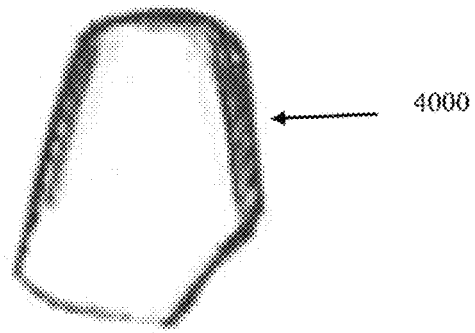
FIG. 15C is a perspective view a toe cot made from a disposable transfer medium gas-permeable membrane.

The anti-inflammatory agent as shown in FIG. 13 is created by sonicating the anti-inflammatory agent in the perfluorocarbon liquid. An example of a typical preparation of the mixture is to take the 10 mg of Sigma A5376 Acetylsalicylic acid powder 2000 and placing it in a 300-ml suitable glass container such as a beaker 2010. The add 200 ml of perfluorodecalin 2020 but any perfluorocarbon liquid described can be used. The place the sonicator tip of a Branson Sonifier 450 so that it extends to approximately 2 mm from the bottom of the beaker. Set the power supply for controls accordingly to 20% Duty Cycle, Output control to 6 and timer to 8. Cover the beaker with a piece of film to prevent splatter or contamination and sonicate for 20 minutes. The sonification can also be completed in other devices such as placing the glass container in a Branson HT50 ultrasonic bath cleaner and sonicating the mixture until all the powder of the anti-inflammatory agent is suspended in the perfluorocarbon liquid and is not in contact with the bottom of the glass container. Taking the mixture then place it in a vial 2030 for coating the infected surface. The container material is specifically selected to be made from glass to minimize any contamination from the container.

Figure 5A:
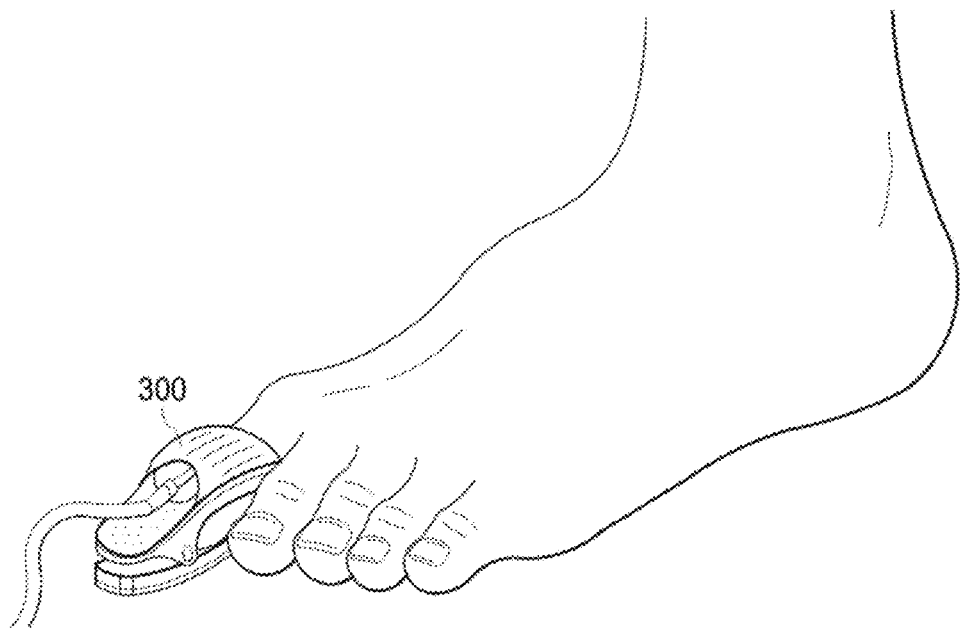
FIG. 5A is a perspective view of an exemplary toe-clip applicator in accordance with the disclosure.
Figure 5B:
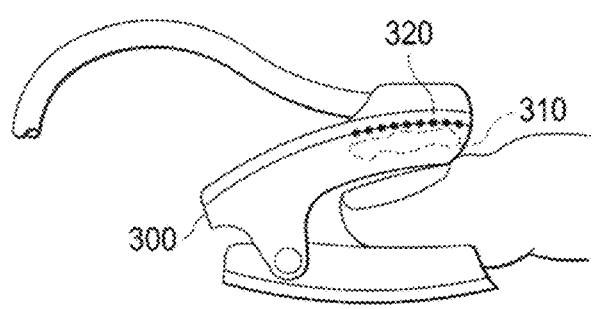
FIG. 5B is a partial cross-sectional view of the exemplary toe-clip applicator shown in FIG. 5A.

In one embodiment, perfluorodecalin liquid with anti-inflammatory agent is pre-applied to the infected nail to act as a redox gas facilitator substance. As shown in FIGS. 5A and 5B, a toe-clip 300 incorporating a plasma-generating device 320 is then attached to the infected toe and a 30-minute treatment protocol is initiated which generates antifungal gases 310 using electrical energy and air. This treatment may be performed as a series of successive treatments to improve the aesthetic appearance of the nail, destroy the fungal infection and promote healthy nail growth. The perfluorodecalin with anti-inflammatory agent enhances the gas exchange between the nail bed and the plasma-generating device and allows the antifungal gas to more effectively penetrate the dense nail plate, the anti-inflammatory agent helps reduce the inflammation in the surrounding tissue due to the proximal infection and or the curative gasses.

Figure 6:
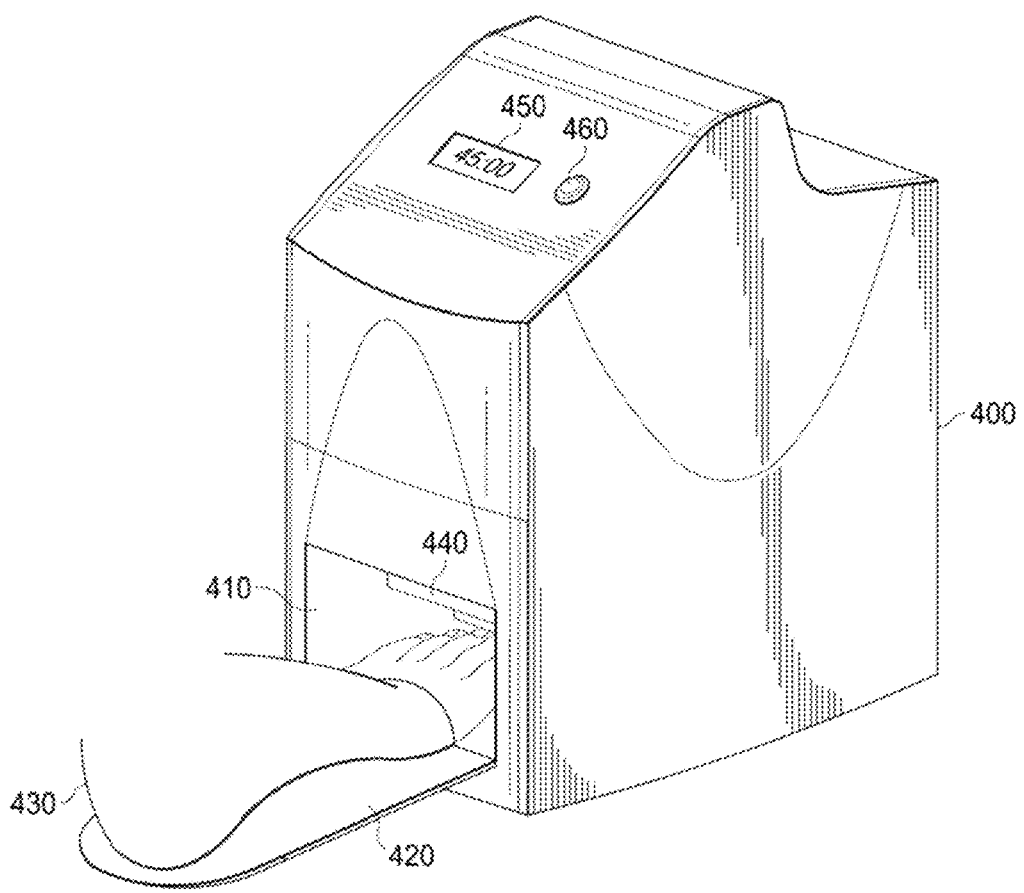
FIG. 6 is a perspective view of an alternate exemplary treatment system embodiment in accordance with the disclosure.

In another exemplary embodiment, a pre-made redox gas solution may be applied to a treatment area and additional treatment can be applied through the use of a non-thermal plasma treatment, thus replenishing or adding additional species of redox gas to the treatment area. As shown in FIG. 6, a plasma-generating device 400 may include a chamber 410 having a lid or door 420, within which chamber a foot 430 may be placed for treatment proximate a plasma source 440. The plasma may be provided for a predetermined amount of time using a control circuit including a timer 450 that is activated by pressing a start/stop button or switch 460.

In another exemplary embodiment, the method includes coating the affected nail(s) along with the entire foot with the pre-made redox gas solution and subjecting the entire foot to curative gasses, in order to destroy pathogens thereon and help prevent reinfection of the nail by pathogens residing elsewhere on the foot. The anti-inflammatory agent incorporated into the is helpful for both inflammations due to the proximal infection or from the effect of exposure to the curative gasses.

The redox gas solutions used during treatment may provide a means for delivering a stable solution of an oxidation or reduction gas in its most active, non-hydrolyzed state. In addition, the redox gas solutions may offer the advantage of providing a very low surface tension medium (generally on the order of approximately 15 dynes/cm), thereby enabling the oxidizing gas solution to efficiently contact and thoroughly penetrate a nail or skin infection as well as reducing any associated inflammation.

Additionally, the PFC can act as a gas facilitator by providing an improvement in gas exchange between a non-thermal plasma device that creates in situ an antimicrobial gas and the nail barrier where the microbe resides. The PFC enhances the capacity of an active fungicidal gas to effectively penetrate the keratin matrix of fingernails and toenails such as to produce therapeutically relevant concentrations even in deeper regions of the matrix.

As shown in FIGS. 7-12, an exemplary embodiment of a system for treating onychomycosis is described. A main body housing 500 includes a chamber assembly 510, a power supply assembly 520, a shield assembly 530, an electronics panel assembly 540, and a rear cover assembly 550.

The main body housing 500 further may include an on/off button 560 for overall control of system operation. A display 570 disposed on the top of the main body housing 500 may provide desired information related to system operation. By way of example only, and without limitation, the display 570 may show a countdown timer reflecting the time remaining in a treatment session. Further, the main body housing 500 may include a handle 580 to help promote positioning of the system for a treatment session.

Figure 9:
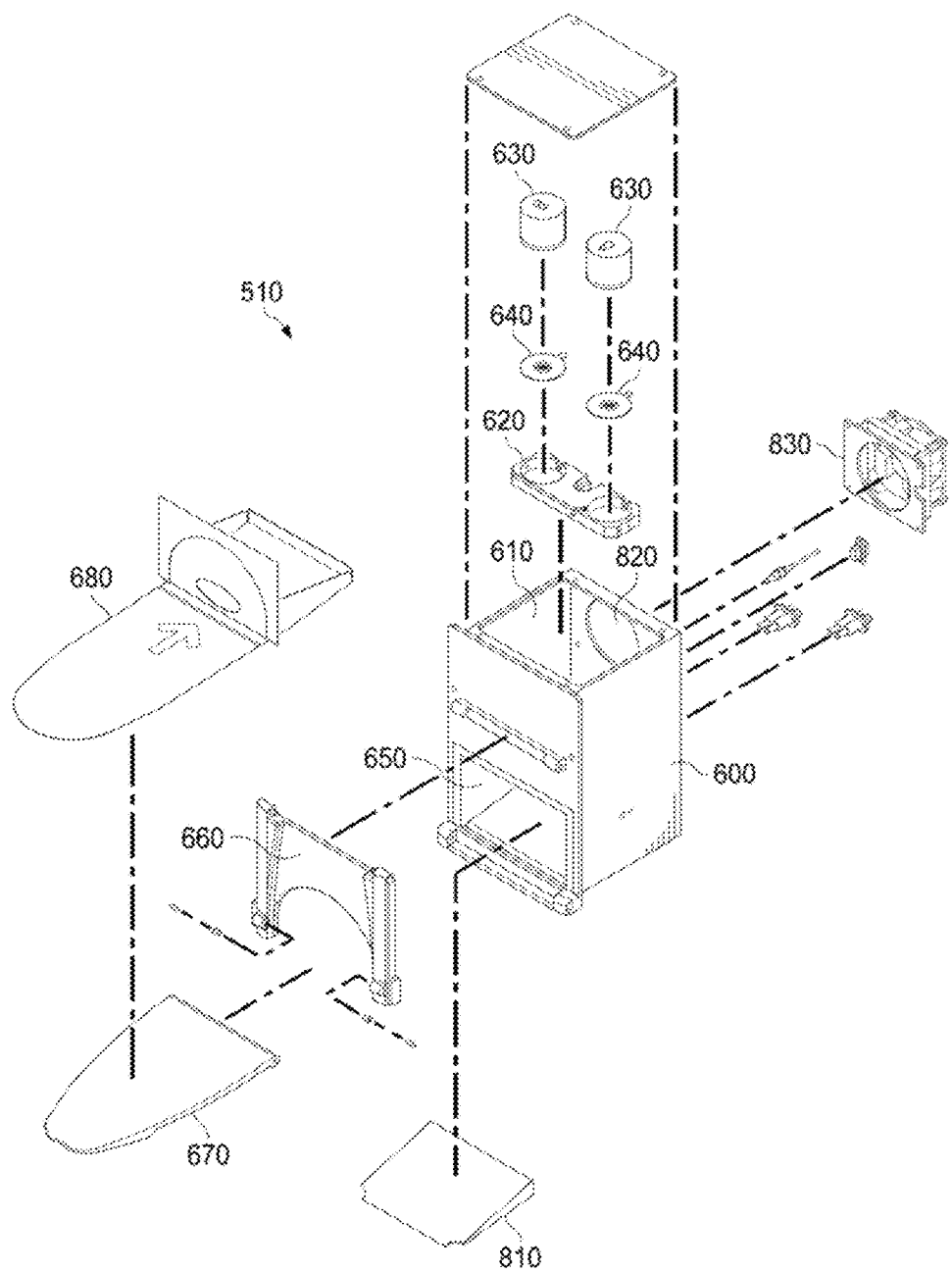
FIG. 9 is an assembly view of the chamber housing of the exemplary treatment system shown in FIG. 8.
Figure 10:
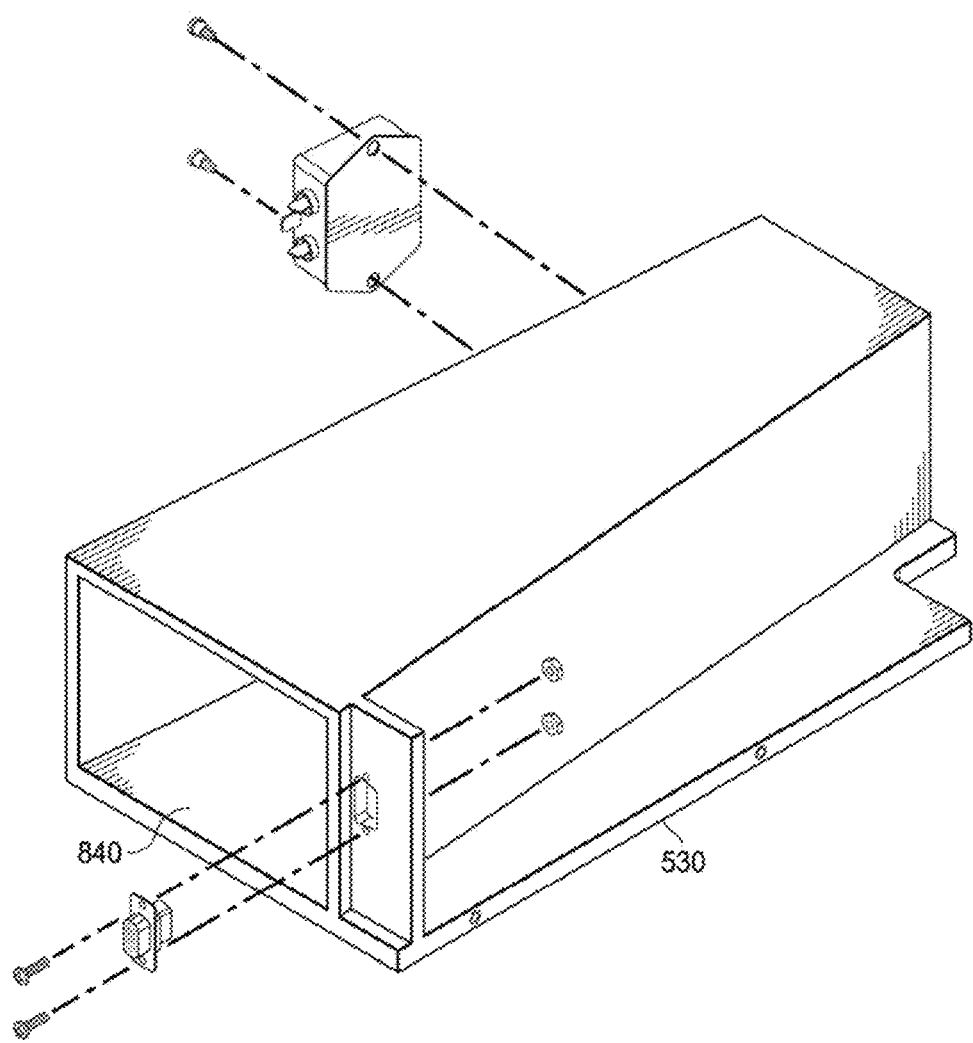
FIG. 10 is an assembly view of the exhaust duct of the exemplary treatment system shown in FIG. 8.
Figure 11:
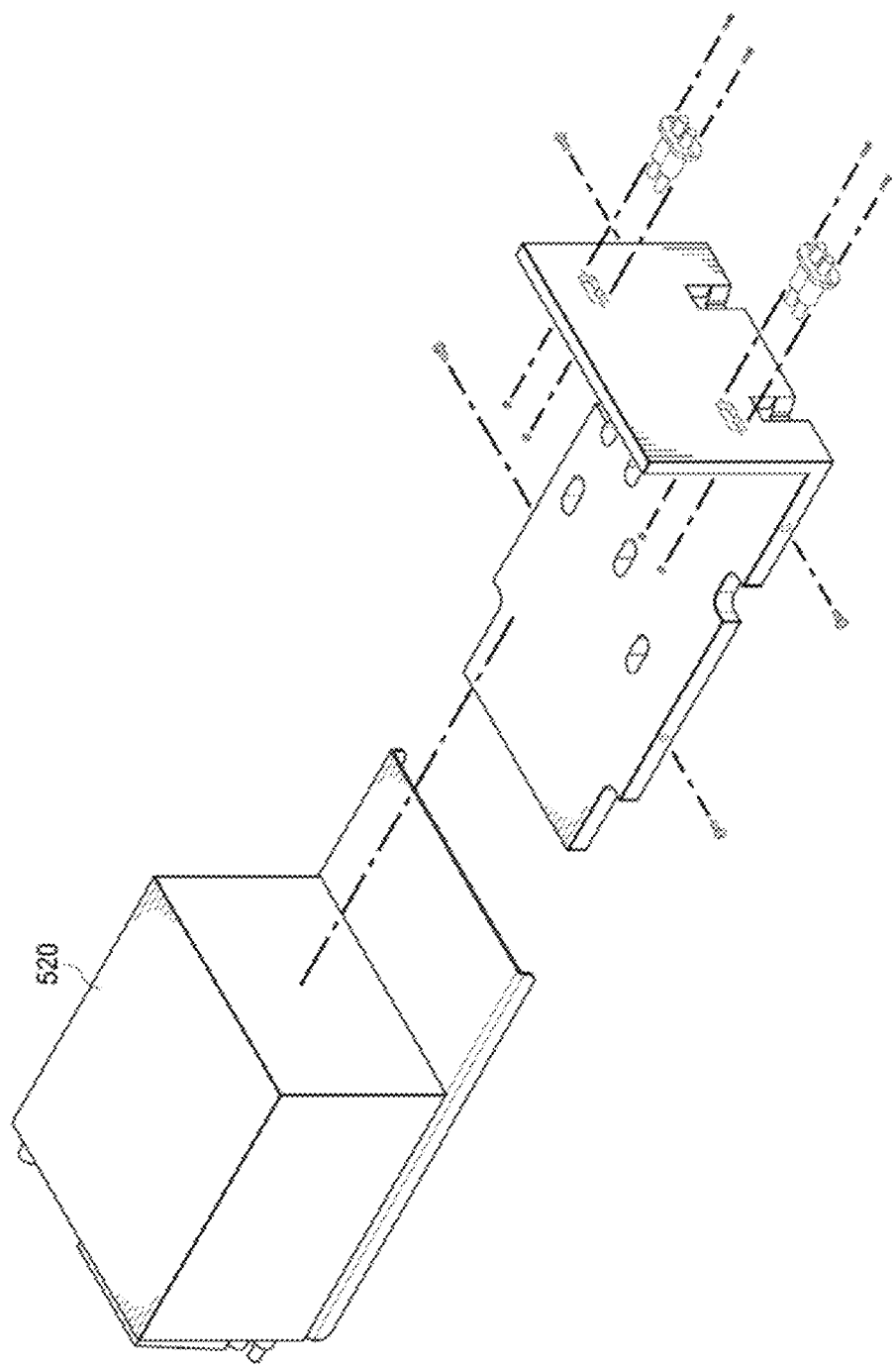
FIG. 11 is an assembly view of the power supply housing of the exemplary treatment system shown in FIG. 8.

The chamber assembly 510 is shown in greater detail in FIG. 9. A chamber assembly housing 600 includes a chamber 610 disposed therein. A plasma head holder 620 disposed within the chamber generally positions a pair of plasma head assemblies 630 in the upper portion of the chamber 610. A plasma head assembly 630 may have a UV filter 640 disposed proximate the holder 620. The housing 600 includes an opening 650 at the lower front portion of the housing 600. A chamber hatch cover 660 may be hingedly attached to the housing 600 above the opening 650, so that the cover 660 may be rotatable downwardly to a lower position covering at least a portion of the periphery of opening 650. A foot ramp 670 may be hingedly attached to the housing 600 below the opening 650, so that during system non-use the ramp 670 may be rotatable upwardly to an upper position covering the cover 660 and opening 650.

In operation, the system includes use of a disposable liner 680. See FIGS. 9 and 12A and 12B. The liner 680 includes a tray portion 690 including a base 700, a back wall 710, and two side walls 720, 730. The liner 680 may be provided in a flat configuration (see FIG. 12A) and then be folded into a final configuration for use (see FIG. 12B).

The base 700 proximately corresponds in size and shape to the size and shape of the bottom of chamber 610. The front of tray portion 690 includes a perimeter support 740 and a film/covering 750. The support 740 and film/covering 750 are larger in peripheral size and shape as compared to the peripheral size and shape of the opening 650. In that way, the front of tray portion 690 may be held in place over the opening 650 and between the cover 660 and the front of housing 600 when the cover 660 is rotated into its lower position. In this position, the base 700 covers the bottom of chamber 810, and the back wall 710 and side walls 720, 730 cover at least part of the lower ends of the back and side walls of chamber 610; and a seal is provided to help prevent during treatment the escape of gases from the chamber 610 at the periphery of opening 650.

The liner 680 may include a sheet 760 extending forward from the base of the front of tray portion 690. In one embodiment, the sheet 760 proximately corresponds in size and shape to the foot ramp 670. The sheet 760 may help to prevent contact between the treatment system and the foot 780 of a patient undergoing treatment. See FIG. 7.

Figure 7:
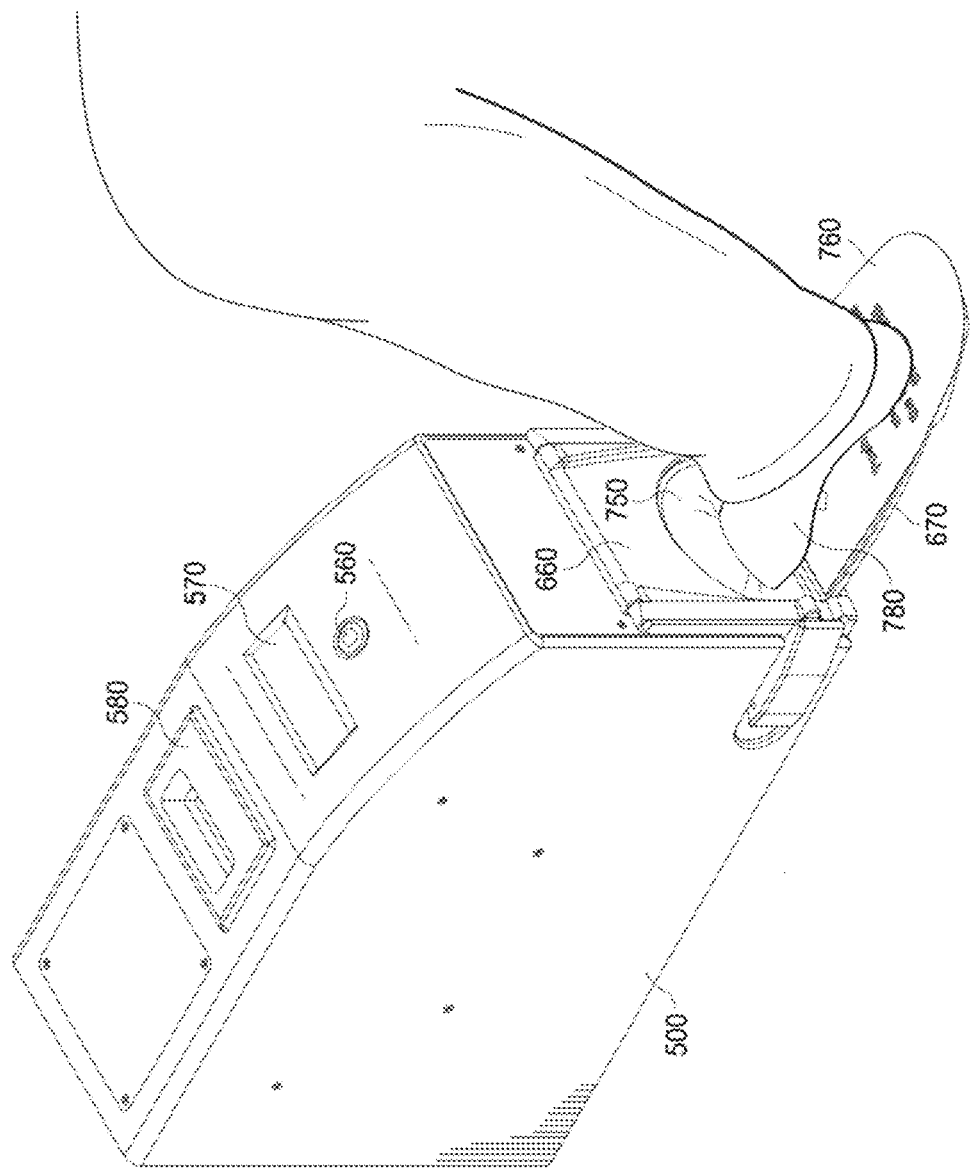
FIG. 7 is a perspective view of another alternate exemplary treatment system embodiment in accordance with the disclosure.
Figure 8:
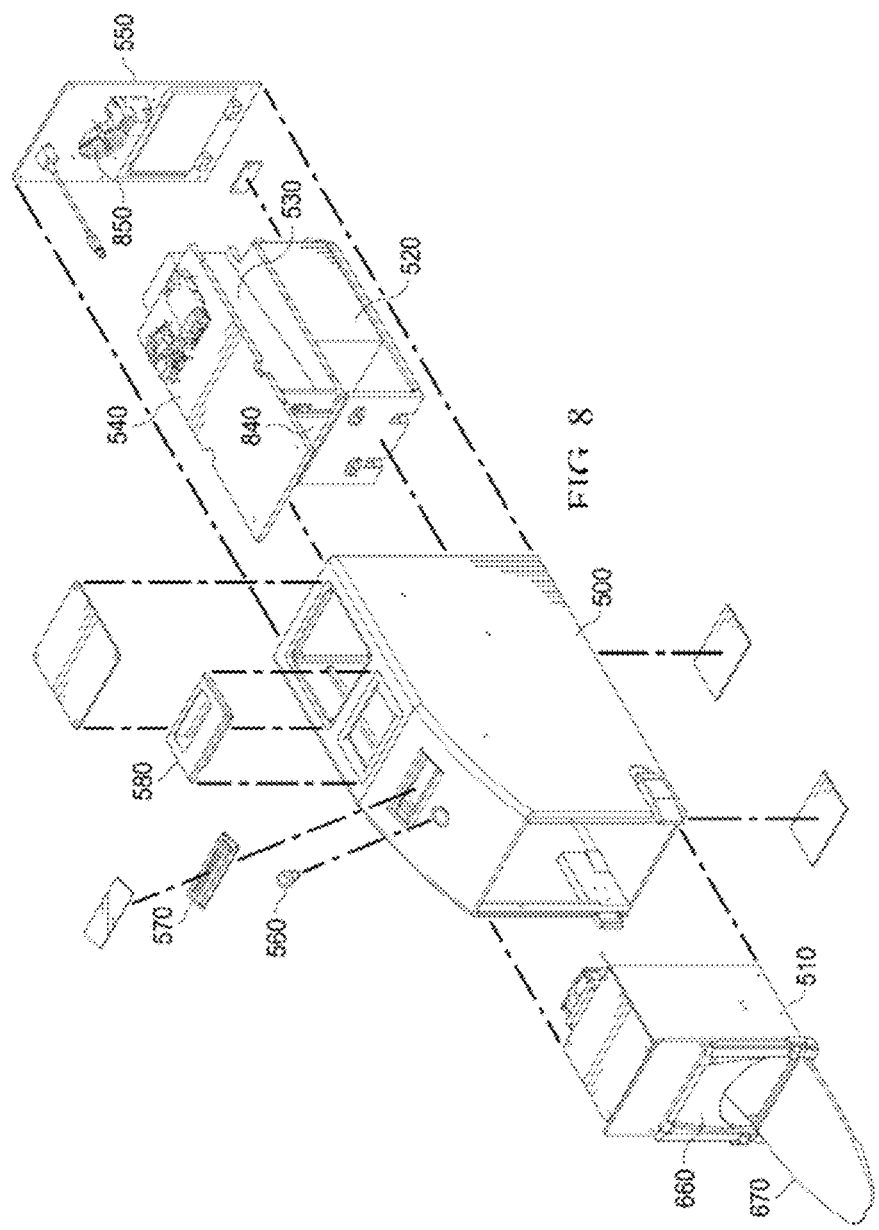
FIG. 8 is an assembly view of the exemplary treatment system shown in FIG. 7.
Figure 12A:
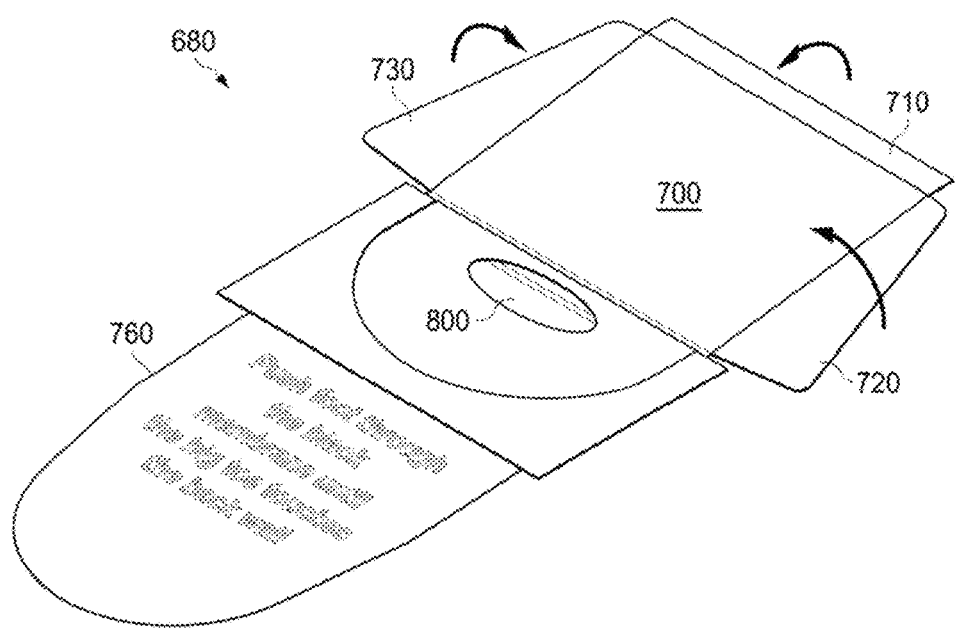
FIG. 12A is a perspective view of a disposable tray of the exemplary treatment system shown in FIGS. 7 and 9.
Figure 12B:
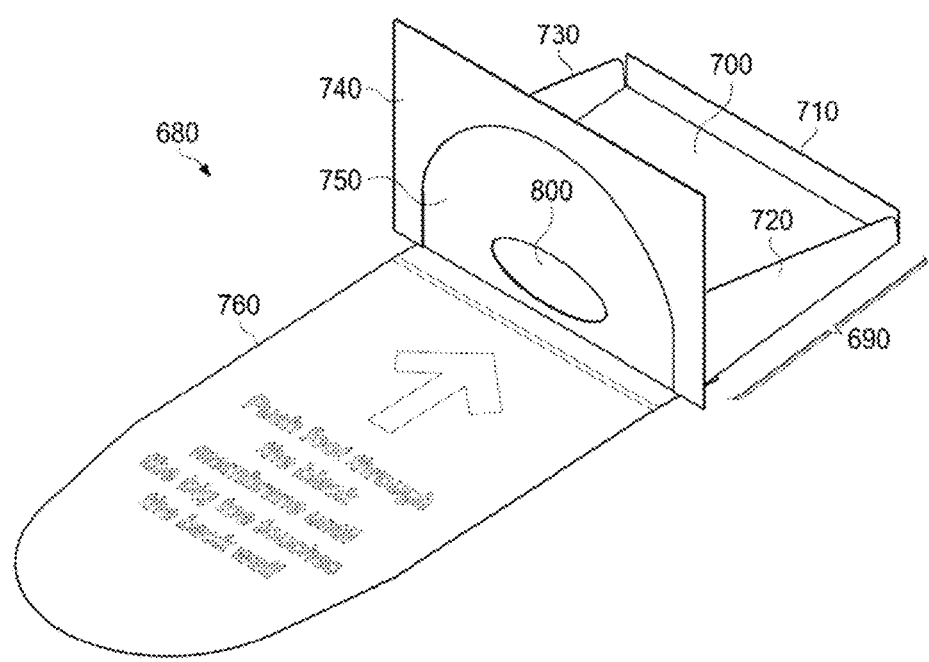
FIG. 12B is a perspective view of a disposable tray in a folded configuration for use in the exemplary treatment system shown in FIGS. 7 and 9.

As illustrated in FIGS. 7, 12A and 12B, the film/covering 750 includes a port 800 therein. The port 800 may be sized and shaped so that a foot 780 may be inserted in part therethrough. In that way, the film/covering 750 acts as a seal about the foot 780 to help prevent the escape of gases from the chamber 610 during treatment.

To help position the foot within the chamber 610, a wedge 810 may be removably placed at the bottom of chamber 610 below the tray portion 690. For 24 mm high toes a 4.5 degree wedge may be used. For 18 mm high toes an 8.5 degree wedge may be used. In one embodiment, during treatment the distance between the top of the toes and a plasma head assembly 630 may be approximately 15 mm. In one embodiment, the wedge 810 may be separate from the tray portion 690. In another embodiment, the wedge 810 may be formed with the tray portion 690, e.g., at the base 700.

In yet another embodiment, the wedge 810 may be formed by folding flat material to provide a wedge 810 of a desired size and shape to help position the foot within the chamber 610.

The rear wall of the housing 600 may include an exhaust port 820. Mounted to the outside of housing 600 at exhaust port 820 may be an exhaust fan 830. In one embodiment, during the final 15 seconds of a treatment period the exhaust fan 830 turns on automatically to help empty the chamber 610 of any active gases. Activated gases may be directed by the fan 830 from chamber 610 through a carbon filter disposed in exhaust duct 840 of shield assembly 530. See FIG. 10. Deactivated gases then may exit the exhaust duct 840 at exit port 850 of rear cover assembly 550.

During operation, the plasma head assemblies 630 transfer their energy onto a patient's nail through diffusion of the plasma constituents. These constituents flow like a gas within the chamber 650. This action provides a controlled bathing of the nail in plasma energy at a low thermal profile. The typical temperature in the treatment chamber 650 may be 31-26° C. (89-79° F.) after a 45-minute treatment.

The disposable liner 680 may be single use only and help prevent cross contamination between patients by covering areas of the system that may come in contact with a patient's foot. The liner 680 includes a box-like tray portion 690 that may be made of medical grade APET plastic (polyester). The film/covering 750 and sheet 760 may be made of medical grade linear low density polyethylene, and may be latex free to avoid biocompatibility or allergy issues. The disposable liner 680 may be locked in place in the system prior to insertion of a patient's foot through the opening or port 800 in film/covering 750.

Referring to FIGS. 2, 9, 13, 14, the disposable transfer medium gas-permeable membrane 3000 is installed within the treatment chamber and on a dispensing reel 3100 and take-up reel 3200 and is exposed inside chamber 510. Dispensing reel 3100 includes a perfluorocarbon dispenser 3300 such as a syringe which dispenses perfluorocarbon with anti-inflammatory agent in the perfluorocarbon liquid 3400 onto the membrane 3000. The membrane is positioned between one or more reactive species generators and the infected body part such as toes of the inserted foot or nails of the hand within chamber 510. With each insertion of infected body part the take-up reel 3200 is engaged by turning handle 3210 pulling membrane 3000 to position a clean section of membrane 3000 into chamber assembly 510. As the membrane 3000 advances pass perfluorocarbon dispenser 3300 the operator dispenses perfluorocarbon with anti-inflammatory agent in the perfluorocarbon liquid 3400 onto the membrane 3000 by depressing the plunger of the syringe of perfluorocarbon dispenser 3300 so that the perfluorocarbon liquid 3400 is imbibed or saturated into the membrane 3000. The membrane is then in position so that it contacts the infection on the patient's body part i.e. surface 90 of nail/tissue 100. During operation of the plasma head assemblies 630 transfer their energy onto a patient's infection through diffusion of the plasma via the perfluorocarbon with anti-inflammatory agent in the perfluorocarbon liquid 3400 which has been applied to the membrane 3000 such that the perfluorocarbon liquid 3400 is imbibed or saturated into the membrane 3000 and is in communication with the infected body part. The plasma forms reactive species 60, 70. The reactive species 60, 70 dissolve in a perfluorocarbon liquid 80 applied to the membrane 3000 which is in communication with the surface 90 of nail/tissue 100. The redox gas solution including reactive species 60, 70 diffuses into the nail/tissue bed to eradicate fungus located therein. These reactive species 60, 70 flow like a gas within the chamber 650. This action provides a controlled bathing of the nail in plasma energy at a low thermal profile. The typical temperature in the treatment chamber 650 may be 31-26° C. (89-79° F.) after a 45-minute treatment.

Referring to FIGS. 2, 9, 13, 14, 15A, 15B and 15C, a toe cot 4000 made from a disposable transfer medium gas-permeable membrane 4050 is placed on the toe 4075 with the infection and the gas-permeable membrane 4050 is in communication with the infection 4200. This cot replaces the disposable transfer medium gas-permeable membrane 3000 of FIG. 14. The perfluorocarbon with anti-inflammatory agent 4100 is applied to the transfer medium gas-permeable membrane 4050 so that the perfluorocarbon liquid 4100 is imbibed or saturated into the membrane 4050. The perfluorocarbon with anti-inflammatory agent 4100 is applied so that it is in communication with the with the infection 4200 and transfer medium gas-permeable membrane 4050. The toe 4075 with the infection 4200 is placed in chamber 660 which contains plasma head assemblies 630. The plasma head assemblies 630 uses electrical energy and a preselected gas (typically air, argon or helium) to create electric fields, energetic electrons and favorable chemistry for antimicrobial therapy. During operation, the plasma head assemblies 630 transfer their energy onto a patient's nail through diffusion of the plasma constituents. These constituents flow like a gas within the chamber 650. This action provides a controlled bathing of the nail in plasma energy at a low thermal profile. The gas-permeable membrane 4050 that forms the toe cot 4000 is position so that it contacts the infection 4200 on toe 4075 and anti-inflammatory agent 4100 imbibed or saturated into the membrane 4050 is in communication with infection 4200. During operation of the plasma head assemblies 630 transfer their energy onto a patient's infection through diffusion of the plasma via the perfluorocarbon with anti-inflammatory agent in the perfluorocarbon liquid 4100 which has been applied to the membrane 4050. The plasma forms reactive species 60, 70. The reactive species 60, 70 dissolve in a perfluorocarbon liquid 4100 applied to the gas-permeable membrane 4050 that forms the toe cot 4000 which is in communication with the infection 4200 on toe 4075. The redox gas solution including reactive species 60, 70 diffuses into the nail/tissue bed to eradicate fungus located therein. These reactive species 60, 70 flow like a gas within the chamber 650. This action provides a controlled bathing of the nail in plasma energy at a low thermal profile. The typical temperature in the treatment chamber 650 may be 31-26° C. (89-79° F.) after a 45-minute treatment.

For convenience only, and without limitation, reference is made herein to treatment of a foot. Of course, other areas may be treated as well, e.g., the hand, an ear, a wound, etc. Accordingly, for some treatments the perfluorocarbon coating will not be placed within a chamber, but will coat all or a portion of a chamber's walls.

For convenience only, and without limitation, reference is made perfluorodecalin solution or perfluorocarbon solution herein. As defined in the instant invention these solutions all include an anti-inflammatory agent.

The invention can also be used to treat other parts of the body such as the ear for an ear infection. Here the anti-inflammatory agent provides the similar benefits as it does when treating a hand or foot infection by helping to reduce any inflammation to associated tissue. For example, when used to treat an inner ear infection, to help position plasma gas within the ear canal, an ear probe may be positioned over the plasma generator head. The ear probe may include a tapered, generally conical, concavely curved outer surface that may be formed of a soft thermal insulator such as foamed polyurethane. The ear probe may be adapted to engage the ear canal of a subject. Perfluorocarbon, e.g., perfluorodecalin solution with anti-inflammatory agent, may be added to the ear chamber. A disposable protective cap may be placed over the ear probe that contains a UV filter screen for blocking UV light produced by the plasma device. The disposable protective cap both blocks UV light and helps to maintain hygiene. Upon activation, plasma gas comes out of the device, through the UV filter screen and fills up ear chamber for ear infection treatment. In one embodiment, during treatment the distance between the ear's tympanic membrane and a plasma head assembly may be approximately 5 mm.

By way of further example, forming a wound chamber about a wound treatment site may enable the precise treatment of wounds with a plasma environment. A flexible, impermeable barrier may be secured to healthy skin about a wound to form a wound chamber. Upon enclosure of the wound within the chamber, a micro-environment may be created isolating the wound from the surrounding non-sterile environment. The wound chamber thus may serve as a precise plasma delivery platform, with perfluorocarbon and anti-inflammatory agent (e.g., perfluorodecalin) added to the wound.

EXAMPLES

The following examples are offered to aid in a better understanding of the present invention. These examples are not to be construed as an exhaustive compilation of all embodiments of the present invention and are not to be construed as limiting the scope thereof.

First the anti-inflammatory agent is created by sonicating the anti-inflammatory agent in the perfluorocarbon liquid. An example of a typical preparation of the mixture is to take the 10 mg of Sigma A5376 Acetylsalicylic acid powder and placing it in a 300-ml suitable glass container such as a beaker. The add 200 ml of perfluorodecalin but any perfluorocarbon liquid described can be used. The place the sonicator tip of a Branson Sonifier 450 so that it extends to approximately 2 mm from the bottom of the beaker. Set the power supply for controls accordingly to 20% Duty Cycle, Output control to 6 and timer to 8. Cover the beaker with a piece of film to prevent splatter or contamination and sonicate for 20 minutes. The container material is specifically selected to be made from glass to minimize any contamination from the container. The mixture is suitable mixed when none of the powder is sitting on the bottom of the glass container. Taking the mixture then place it in a vial for coating the infected surface.

Eradication of *T. rubrum* Through a Bovine Hoof Using Perfluorodecalin (PFD) Facilitator and an SMD Plasma-Generating Device.

The in vitro test model uses a bovine hoof disk, a surrogate nail model established in the literature. It is used along with a modified Franz-type diffusion cell to isolate the fungal contaminated side of the hoof in an enclosed chamber that ensures the treatment path is through the hoof barrier. An equal amount of *T. rubrum* is pipetted onto each hoof disc consisting of a 100 ul suspension. Each hoof disk is then placed fungus side down into the modified Franz cell and sealed with an O-ring. Each hoof is then plasma treated for 45 minutes where the average thickness of hoof disks is 0.35 mm. Eight hoof disks were treated as:

a. Control that is placed directly into the wash tube without any treatment.
b. Two PFD-only hoofs had 100 ul PFD pipetted directly onto the hoof opposite side from the fungus. This was allowed to sit for 45 minutes in the hood before placing in the wash tube.
c. Two Plasma treatment only hoofs get just a 45 minute plasma treatment.
d. Three Plasma treatment with PFD hoofs had 100 ul PFD pipetted directly onto the hoof opposite side from the fungus immediately before applying plasma treatment (i.e., while wet).

After treatment, each hoof went through a fungal collection protocol consisting of washing, dilution, plating and incubation. The results after seven days of incubation was a colony count of about 24,000,000 from the control hoof plate. The two hoofs that were treated with PFD-only had colony reductions of 7% and 28% compared to control. The two hoofs that were treated with 45 minutes of plasma only had colony reductions of 84% and 88% when compared to control and quite unexpectedly the three hoofs that were treated with both PFD and 45 minutes of plasma treatment showed a colony reduction of 94% for one hoof and no colonies or 100% and 100% reductions for the other two hoofs.

Application of PFC onto the Skin/Nail

The contacting of the infected area with the perfluorocarbon can occur by various means. The perfluorocarbon can be applied with a dropper, foam tip swab, a cotton tip swab or a sponge applicator. It may be sprayed or squeezed on in a foam or gel formulation.

A further apparatus for contacting the infected area with a perfluorocarbon consist of a gas-permeable membrane that includes perfluorocarbon liquid in its composition imbibed or saturated in the membrane and allows for the rapid, enhanced and uniform transfer of plasma reactive species between the plasma device and the infection. The contacting of the infection with the perfluorocarbon membrane (e.g., a dressing, bandage, patch, etc.) may define the treatment site. The gas permeable membrane composition comprises at least one material selected from ceramics, polymers, woven substrates, non-woven substrates, polyamide, polyester, polyurethane, fluorocarbon polymers, polyethylene, polypropylene, polyvinyl alcohol, polystyrene, vinyl, plastics, metals, alloys, minerals, non-metallic minerals, wood, fibers, cloth, glass, and hydrogels. In one embodiment, the membrane barrier is a silicone composition that contains an effective amount of perfluorocarbon and acts as a dressing. For nail treatment, the membrane may be manufactured in a toe or finger cot shape that may be slipped easily over the infected digit, Loading PFC with Antifungal Gas A PFC may be loaded with antifungal gas in a manufacturing facility. Alternately, a home-use device may be provided so that a patient may "load" the PFC at their home, then apply it to their toenails. The loading can be done with a plasma device, and/or a pure gas canister (NO, ozone, $H_2O_2$, etc.), etc. before treatment application by the patient at home. As described, there are other ways of loading the PFC with antifungal gas after it is applied to the infections site (e.g., besides a plasma device). In one embodiment, a pure gas canister (NO, ozone, $H_2O_2$, etc.) may be used. In another embodiment, a secondary chemical reaction may create the gas. Redox gases can be purchased in their gaseous form but have relatively high vapor pressure, require expensive sealed and pressurized tanks for storage. To provide handling convenience and cost-effectiveness, redox reagents are often created in an aqueous solution such as hypochlorous acid (generated from sodium hypochlorite), hydrogen peroxide, or nitric acid. These aqueous solutions are, however, less reactive than their gaseous counterparts, often requiring elevated temperatures and significant time to complete the redox reaction in situ.

Again, a redox gas may be added to a perfluorocarbon liquid by any conventional technique (e.g., sparging or gas injection or simple diffusion) to create a redox gas solution. A typical sintered sparger can be purchased from Mott corporation http://mottcorp.com. Such redox gas solutions provide a means for delivering a stable solution of an oxidation or reduction gas in its most active, non-hydrolyzed state that also allows handling convenience and cost-effectiveness.

Sterilization and Other Therapies

Use of the described system and method also may promote wound sterilization and healing, may treat ear infections, may improve the sterilization of medical devices, may treat dental infections, may treat acne and various other dermatological infections, may promote bleeding cessation, may improve hand disinfection hygiene, or may treat skin, esophagus or colon cancer. It can also be used in veterinarian animal health for all such described applications.

In one embodiment, a method of sterilizing or decontaminating an item comprises the steps of: (a) coating the item to be sterilized with a perfluorocarbon liquid layer to allow the perfluorocarbon liquid to come in close proximity with the item; (b) generating a gaseous plasma around the item, such that both the liquid perfluorocarbon and the exterior of item is exposed to reactive components of said plasma; and (c) maintaining the item in said plasma for a time period sufficient to allow the active sterilizing species generated from the plasma to effect sterilization and destroy any microorganisms present.

In another embodiment, decontamination of a liquid or gas may occur using a PFC including a reactive species. Examples include, without limitation, using the PFC/reactive species solution to eliminate microbes in blood with the aid of a dialysis machine, and to improve the sterilization of air using conventional methods.

It should be understood that the foregoing description is only illustrative of the invention. Various alternatives and modifications can be devised by those skilled in the art having the benefit of this disclosure, without departing from the invention. Accordingly, the invention is intended to embrace all such alternatives, modifications and variances.

Certain exemplary embodiments of the disclosure may be described. Of course, the embodiments may be modified in form and content, and are not exhaustive, i.e., additional aspects of the disclosure, as well as additional embodiments, will be understood and may be set forth in view of the description herein. Further, while the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention.

We claim:

1. A method of treating an infection on a body part comprising the steps of a) preparing an anti-inflammatory perfluorocarbon liquid comprising an anti-inflammatory agent suspended in a perfluorocarbon liquid by placing said anti-inflammatory agent into a glass container of perfluorocarbon liquid and then sonicating until the anti-inflammatory agent is suspended in the perfluorocarbon liquid, b) applying said anti-inflammatory perfluorocarbon to a gas-permeable membrane such that it is imbibed into the membrane, c) applying said gas-permeable membrane to said body part with an infection, d) positioning said body part in a chamber, e) positioning a plasma head assembly comprising an electrical control circuit, a high voltage electrode, and a ground electrode disposed within said chamber such that the plasma head assembly is in communication with said gas permeable membrane and such that said body part is proximal and in communication with said plasma head assembly wherein said plasma head assembly is capable of forming a plasma reactive species proximate to said ground electrode, and f) producing a reactive species from said plasma head, which is in communication with said anti-inflammatory perfluorocarbon imbibed gas-permeable membrane.

2. The method of claim 1, wherein the anti-inflammatory agent is selected from the group consisting of aspirin, acetylsalicylic acid, salicylic acid, celecoxib, diclofenac, diflunisal, etodolac, ibuprofen, ketorolac tromethamine, indomethacin and drugs that meet the definition of NSAIDs.

3. The method of claim 1, wherein the perfluorocarbon liquid is selected from the group consisting of fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanes, fluoropropanes, fluoroethers, fluoropolyethers, fluorotributylamines, fluorotriethylamines, perfluorohexanes, perfluoropentanes, perfluorobutanes, perfluoropropanes, sulfur hexafluoride, methylperfluorobutylether and perfluoro(tert-butylcyclohexane).

4. The method of claim 1, wherein the gas-permeable membrane is selected from the group consisting of ceramics, polymers, woven substrates, non-woven substrates, polyamide, polyester, polyurethane, fluorocarbon polymers, polyethylene, polypropylene, polyvinyl alcohol, polystyrene, vinyl, plastics, metals, alloys, minerals, non-metallic minerals, wood, fibers, cloth, glass, and hydrogels.

5. A method of treating an infection on a body part comprising of: a) preparing an anti-inflammatory perfluorocarbon liquid comprising of an anti-inflammatory agent suspended in a perfluorocarbon liquid by placing said anti-inflammatory agent into a glass container of perfluorocarbon liquid and then sonicating until the anti-inflammatory agent is suspended in the perfluorocarbon liquid, b) applying said anti-inflammatory perfluorocarbon to a gas-permeable membrane formed into a cot such that it is imbibed into the membrane of the cot, c) applying said cot formed from the gas-permeable membrane to said body part with an infection, d) positioning said body part in a chamber, e) positioning a plasma head assembly comprising an electrical control circuit, a high voltage electrode, and a ground electrode disposed within said chamber such that the plasma head assembly is in communication with said gas permeable membrane and such that said body part is proximal and in communication with said plasma head assembly wherein said plasma head assembly is capable of forming a plasma reactive species proximate to said ground electrode, and f) producing a reactive species from said plasma head, which is in communication with said anti-inflammatory perfluorocarbon imbibed gas-permeable membrane.

6. The method of claim 5, wherein the body part is selected from the group consisting of hand, foot, toe and finger.

7. The method of claim 5, wherein the anti-inflammatory agent is selected from the group consisting of aspirin, acetylsalicylic acid, salicylic acid, celecoxib, diclofenac, diflunisal, etodolac, ibuprofen, ketorolac tromethamine, indomethacin and drugs that meet the definition of NSAIDs.

8. The method of claim 1, wherein the perfluorocarbon liquid is selected from the group consisting of fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanes, fluoropropanes, fluoroethers, fluoropolyethers, fluorotributylamines, fluorotriethylamines, perfluorohexanes, perfluoropentanes, perfluorobutanes, perfluoropropanes, sulfur hexafluoride, methylperfluorobutylether and perfluoro(tert-butylcyclohexane).

* * * * *